(12) United States Patent
Anderson

(10) Patent No.: US 12,377,109 B2
(45) Date of Patent: Aug. 5, 2025

(54) FORMULATION AND NONCOVALENT STABILIZATION OF OLIVETOLIC ACID DERIVATIVES

(71) Applicants: David Anderson, St. Paul, MN (US); MINGOWOOD PHARMACAL LLC, St. Paul, MN (US)

(72) Inventor: David Anderson, St. Paul, MN (US)

(73) Assignee: Mingowood Pharmacal LLC, Georgetown, SC (US)

( * ) Notice: Subject to any disclaimer, the term of this patent is extended or adjusted under 35 U.S.C. 154(b) by 77 days.

(21) Appl. No.: 18/249,274

(22) PCT Filed: Oct. 15, 2021

(86) PCT No.: PCT/US2021/055142
§ 371 (c)(1),
(2) Date: Apr. 17, 2023

(87) PCT Pub. No.: WO2022/081950
PCT Pub. Date: Apr. 21, 2022

(65) Prior Publication Data
US 2023/0390311 A1 Dec. 7, 2023

Related U.S. Application Data

(60) Provisional application No. 63/093,182, filed on Oct. 17, 2020.

(51) Int. Cl.
| A61K 31/00 | (2006.01) |
| A61K 9/14 | (2006.01) |
| A61K 31/192 | (2006.01) |
| A61P 25/08 | (2006.01) |

(52) U.S. Cl.
CPC ............ *A61K 31/658* (2023.05); *A61K 9/14* (2013.01); *A61K 31/192* (2013.01); *A61P 25/08* (2018.01)

(58) Field of Classification Search
CPC .................................................. A61K 31/658
See application file for complete search history.

(56) References Cited

U.S. PATENT DOCUMENTS

| 9,815,810 B1 | 11/2017 | Ogilvie et al. |
| 11,998,514 B2 * | 6/2024 | Lupia ............... A61K 9/107 |
| 2011/0000632 A1 | 1/2011 | Talma |
| 2012/0093943 A1 * | 4/2012 | Newton ............... A61K 33/26 424/647 |
| 2015/0132407 A1 | 5/2015 | Pennel et al. |
| 2015/0258212 A1 | 9/2015 | Thompson et al. |

FOREIGN PATENT DOCUMENTS

| EP | 3501484 A1 | 11/2021 | |
| WO | WO2019211771 A1 * | 11/2019 | ....... A61K 9/1617 |
| WO | 2020150319 A1 | 7/2020 | |

OTHER PUBLICATIONS

Alexander Beadle, CBDA Vs CBD: What Are the Differences?, Technology Networks, Oct. 18, 2019 (Year: 2019).*

* cited by examiner

*Primary Examiner* — Mark V Stevens
*Assistant Examiner* — Alparslan Asan
(74) *Attorney, Agent, or Firm* — WCF IP

(57) ABSTRACT

Methods of stabilizing acidic cannabinoids by intercalating the acidic cannabinoids into layered double hydroxides (LFHs) are provided. Also provided are compositions comprising the LDH-intercalated acidic cannabinoids, physiologically compatible formulations comprising the compositions and methods of using the formulations to treat a variety of diseases and conditions in subjects.

18 Claims, 8 Drawing Sheets

FORMULATION AND NONCOVALENT STABILIZATION OF OLIVETOLIC ACID DERIVATIVES

CROSS-REFERENCE TO RELATED APPLICATIONS

This application claims benefit of U.S. provisional patent application 63/093,182, filed Oct. 17, 2020, and the complete contents thereof is herein incorporated by reference.

FIELD OF THE INVENTION

This invention is in the field of therapeutic cannabinoids and related compounds derived from olivetolic acid and/or containing decarboxylation-prone 2,4-dihydroxy-6-alkyl-benzoic acid groups in their molecular structure.

DESCRIPTION OF RELATED ART

Deliberate decarboxylation of acidic cannabinoids, for purposes including ease of extraction (e.g., EP1536810A2 to Downs et al.) and to support claims of high CBD (cannabidiol) purity, is the subject of a number of patents as well as standard practice in many CBD production facilities. Yet it is known that carboxylated cannabinoids such as CBDA and THCA possess some useful characteristics and activities that are distinct from, or require significantly smaller doses than, their decarboxylated variants CBD and THC, as exemplified by U.S. Patent Appl. Application #20190117619 to Guy et al. As the unique properties of CBDA in particular become more widely recognized in the various cannabinoid-based industries, commercialization could be severely hampered by the current lack of safe and efficacious formulations of CBDA that exhibit acceptable thermal stability; this is particularly the case for pharmaceutical applications or "medical cannabis products". One particularly important aspect of CBD, the decarboxylated form of the natural phytocannabinoid CBDA, is that CBD has been shown to disrupt the blood-brain barrier [Luo et al., Mol Pharm. 2019 Mar. 4; 16(3):1312-1326], which may permit other cannabinoids to enter the brain but in addition, permits a wide range of poisons to enter the brain that would normally be blocked by the blood-brain barrier.

In particular, the acidic cannabinoids THCA and CBDA have been studied for thermal stability [e.g., see W. Peschel, Sci. Pharm. 2016, 84, 567-584], and both degrade by at least 40% (i.e., 60% retention) during 3 months at room temperature, and during 4 hours at 80° C. In the context of this disclosure, what matters is the shelf-life of the active at or near ambient temperature (or at refrigerator temperatures, for a cold-chain product), which for a pharmaceutical product is typically set just shorter than the timespan over which 10% of the active pharmaceutical ingredient is lost to degradation. Nevertheless, one skilled in the art will recognize that "accelerated stability studies" performed at higher temperatures over shorter periods allow for comparison with published (or otherwise known) studies and are used herein to compare with literature stability studies; these studies can in some cases also be useful in predicting—though not measuring per se—the shelf—lives of products. Wang et al. [Cannabis and Cannabinoid Research, Volume 1.1, 2016, 262-271] reported an activation energy of 115 kJ/mol and a $2.0 \times 10^{12}$ sec$^{-1}$ prefactor in the expression for the degradation rate constant, yielding a half-life for CBDA of 4.06 weeks at 40° C., which is in very good agreement with a Certificate of Analysis from the commercial fine chemical supplier Cerilliant Corporation (Analytical Reference Standards division) for their highly purified CBDA standard solution in acetonitrile; thus Cerilliant reported a 69.8% decrease in potency at 40° C. over 4 weeks [see http://www.cerilliant.com/shoponline/COA.aspx?itemno=8b722e93-d06c-4bf5-91c4-4294235f51d0&lotno=FE04301903]. Citti et al. [Journal of Pharmaceutical and Biomedical Analysis 149 (2018) 532-540] examined CBDA stability in actual hemp oil at elevated temperatures, and noted that their higher degradation rates were probably due to the presence of acids in the oil, with formic acid having a particularly strong effect; the activation energy reported by zCitti et al. was thus lower, 89.5 kJ/mol, and with the prefactor at $6.9 \times 10^8$ l/sec; this yields at half-life at 80° C. of approximately 4.9 hours, for CBDA in hemp oil as extracted. Taking that 30° C. (86° F.) could well represent a temperature that a product (not a cold-chain product) might be exposed to for quite some time in warm climates and in storage facilities, the half-lives of CBDA at 30° C. calculated from different researchers are all quite short by commercial shelf-life standards: 4.5 weeks for Citti et al., 11.6 weeks for Wang et al., and about 12 weeks estimated for the Cerilliant product based on their data; the latter two estimates are in excellent agreement and should be considered much more reliable since the Citti study was performed at higher temperatures and the extrapolation is far less certain. A half-life of, say, 12 weeks is not only hugely problematic from a commercial, 'standardized' product—or for any product standardized or not that claims to feature a significant pharmacologic effect from the carboxylated form of CBDA—but also, by pharmaceutical standards, as coded in FDA guidances and well known in the industry, a degradation of over 10% in about 2 weeks, as implied by these data, would miss the targets of 24, or 18, or even 12 months with <10% loss of potency by a long margin. Strikingly, Peschel has shown that in 40% and 90% ethanol tinctures, even storage in refrigerator conditions (4° C., dark) resulted in over 50% loss of THCA in only 6 months, meaning that even a cold-chain product of acidic cannabinoids is unstable, since 10% loss of potency would be expected in about one month-even if the end user received the product before the one month (from born-on date) and kept it refrigerated except during dosing. One corollary of the rapid degradation of CBDA is that for indications (e.g., nausea, epilepsy, and possibly anxiety) where CBDA is one of the key, if not the key, cannabinoid for treating that indication, the whole idea of a "standardized cannabinoid preparation" or "standardized hemp extract" goes out the window in the face of degradation rates this high.

A number of salts of carboxylic cannibinoids, including ammonia, primary, secondary and tertiary amines, hydrazine, hydroxylamine, and guanidine salts, have been shown to accelerate the decarboxylation of these cannabinoids. See U.S. Patent Application No. US20150038567A1. The objective there is predominantly to "purify" CBD.

Solvents, as well as metal or otherwise catalytic surfaces, can further accelerate the decarboxylation of acidic cannabinoids. Even in the case of true tinctures, Fairbairn, Liebmann and Rowan as early as 1976 reported that concerning solutions of cannabinoids in ethanol, "Previous claims that solutions in ethanol were stable have not been substantiated" [J. Pharm. Pharmacol, 28(1), 1-7]. Glycols, pyridine, nitrobenzene, formamides, chloroform, picoline, amines and acids rather generally, water, and numerous other solvents have been shown to destabilize acidic cannabinoids and/or other beta-hydroxy acids under conditions of inert atmosphere and temperatures between ambient and 140° C.

These issues and others noted herein have greatly hindered any efforts to produce a stable formulation of an acidic cannabinoid, at least without actual covalent modification of the cannabinoid. Covalent modification of a known active compound can be of two general types: a prodrug, or a new drug. A prodrug is generally intended to break down in the body thereby releasing the original drug; the prodrug should show minimal breakdown to the active moiety during its shelf-life in the vial or other container. Typically, the in vivo conversion from prodrug to drug is through the action of an enzyme in the body, leading to higher intersubject and even intrasubject variabilities in absorption and/or strong changes of distribution in the body. As an example of the latter, a water-soluble prodrug of propofol was found to exchange mild pain at the site of injection with instead, a more widespread pain particularly registering in the chest/lung area. Clearly, the toxicity profile and potential target organs of a drug can change, and in fact should well be expected to change, when a drug is covalently modified, and this is particularly true of cannabinoids which are widely known to change activity with nearly any type of covalent change in the molecule, particularly any addition or loss of an atom or chemical group. Whether or not anything (other than administration) changes with a prodrug or any covalent modification, the huge time and monetary expense associated with the regulatory approval of a prodrug—or any New Chemical Entity—must be considered in the decision to covalently modify an existing chemical entity.

Covalent modification of acidic cannabinoids by esterification of the carboxylate group has been reported, with apparent increase in stability, see Pertwee et al. [Br J Pharmacol. 2018 January; 175(1): 100-112]. However, by its very definition, covalent modification creates a New Chemical Entity in terms of regulatory agencies such as the FDA, which is problematic in that the NCE must undergo the full range of toxicity studies, and must be characterized for its ADME properties (Absorption/Distribution/Metabolism/Excretion) and the effects of inter- and intra-subject variabilities in the activities of enzymes that may change the structure of the molecule, such as esterases that can de-esterify an ester of CBDA. Furthermore, chemical modification of hemp and cannabis products is frowned upon in the Supplements/OTC market, where regulations, regulatory guidelines, industry norms, and public opinion are at present strongly calling for 'natural' cannabinoids as extracted from plant material unchanged post-harvest; that is, once the plant (viz., mature bud material) is harvested, there should be minimal chemical modification of the dried and/or extracted material, particularly as concerns covalent modification of the cannabinoids themselves.

Covalent modification of any cannabinoid should not only be suspected to possibly change pharmacologic activity, but should in fact be expected to do so, as anyone with even rudimentary knowledge of the cannabinoids will recognize. Indeed, the carboxylation of CBD to form CBDA appears to increase potency in certain applications (e.g., emesis and epilepsy) by as much as 1,000-fold. Similarly, the shortening of the pentyl side chain of THC to a propyl chain dramatically affects the pharmacologic properties of THC. Such examples abound, and appear to be the rule, not the exception. Thus, the methyl ester of CBDA in Pertwee et al. shows increased thermal stability over CBDA, but also has different pharmacological effects and, naturally, different ADME.

Many routes of administration or consumption have another associated problem with certain cannabinoid-rich extracts: namely, objectionable taste and odor. Many of the cannabinoids are well known to be activators of the TRPV receptors, particularly TRPV1, present in the mouth and nose, so that a "hot", or "spicy-hot" taste and odor result from oral and, particularly, sublingual and buccal administration, increasing in sharpness as the release rate into the tissue increases. They are thus chemical irritants, and other off-tastes and odors are common in hemp and cannabis extracts, and typically the taste will become increasingly objectionable as the extract is concentrated and tissue concentrations increase. 'Boutique' application of these extracts is presently hampered by these off-tastes and odors.

A layered double hydroxide, or LDH, is a natural or (semi-)synthetic clay or clay-like material with the general formula given by: $M^{II}_{1-x}M^{III}_{x}(OH)_2(A^{n-})_{x/n} \cdot mH_2O$, where $M^{II}$=Mg, Co, Ni, Cu, Zn, Ca (as divalent cations); $M^{III}$=Al, Fe, Cr, Ga (as trivalent cations); $A^{n-}$ is an anion such as $CO_3^{2-}$, $NO_3^{-}$, $SO_4^{2-}$, etc., and most commonly x=0.25-0.33. The anion can also be organic, and a number of surfactants have been intercalated into LDHs as the anion, including SDS, SDBS, sulfonates and carboxylates, and others, as well as several drugs, such as ketoprofen. An LDH has a typical anion exchange capacity of ~3.5 meq/gm. U.S. Pat. No. 10,906,859, the complete contents of which is incorporated herein by reference in entirety, describes adamantane carboxylate-intercalated layered double-hydroxide (LDH) particles and the methods of producing adamantane carboxylate-intercalated LDH particles.

U.S. Pat. No. 9,376,367 to Kerkenroth et al. reports methods for producing purified acidic cannabinoids wherein the cation associated with the carboxylic group is selected from the group consisting of $H^+$, $NH4^+$, mono-, di- or trivalent metal ions, primary, secondary, tertiary, or quaternary organic ammonium ions comprising up to 48 carbon atoms, hydrazinium ion ($N2H5^+$) or organic derivatives thereof, hydroxylammonium ion ($NH3OH^+$) or organic derivatives thereof, guanidinium ion ($CN3H6^+$) or organic derivatives thereof, N,N-dicyclohexylamine-$H^+$, N,N-dicyclohexyl-N-ethylamine-$H^+$, and a hydrogenium cation of a pharmaceutical active substance comprising at least one basic nitrogen atom. The stated purpose of these compounds is given in that disclosure: "Hence the invention is based on the objective of providing a process for the production of salts which are as pure as possible, preferably crystalline salts of natural or synthetic cannabinoid carboxylic acids, from which pure neutral cannabinoids can be obtained in a simple manner." Thus, neutral, non-carboxylated cannabinoids are the goal of that invention, and no evidence is given in that disclosure for increased stability of acidic cannabinoids in any reported formulation for human or animal use.

At the time of this writing, the FDA is taking a closer watch on the CBD/hemp supplements area and is necessarily aware of the ultrahigh potency of CBDA—cannabidiolic acid—in several applications and animal models, meaning that eventually it may well rule that CBDA levels in hemp products must be standardized, or at least maintained in a certain concentration range, similarly as with THC in hemp products now. Additionally, it is FDA policy that once a compound is approved as an active ingredient in an FDA-approved drug product, that compound should no longer be sold in the Supplements market, so that the approval of Epidiolex® (highly pure CBD) makes CBD problematic from a legal/marketing perspective.

In this context, the decarboxylation of CBDA in products that are not combusted or vaped (where substantial conversion to CBD is inevitable due to heat and/or light) is problematic not only from a potency point of view but also from a regulatory perspective. It makes no sense to prepare a product with a well-controlled CBDA concentration on the product born-on date when, over a few months shelf life, it degrades substantially. Nor would such be FDA-acceptable as a "standardized" product, as degradation is temperature- and light-dependent and therefore not under control unless expensive cold-chain practices are enforced. U.S. Pat. No. 9,955,716 teaches frozen "ice pop" cannabinoid products that require a cold chain. Current practices and mindsets in the supplements market, and even the dispensaries, do not take favorably to cold chain products due to shelf-space constraints, transportation expenses, customer inconveniences (most of us don't have refrigerators in our cars), and lack of formulation flexibility.

A dearth of methods and materials currently exists also for separation of acidic cannabinoids from neutral components of Cannabis oils (viz., decarboxylated cannabinoids), particularly in view of the instability of the acidics with any heating and with many salt forms.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Compositions achieving benefit from olivetolic acid and its derivatives that are prone to decarboxylation, particularly useful acidic cannabinoids such as CBDA, THCA, and CBGA, need to be found that protect these compounds against decarboxylation rates leading to significant degradation over the shelf-life of the composition; furthermore, the composition should be safe for human and/or pet consumption in one or more mode of delivery, such as sublingual, oral, intranasal, etc. CBDA is known to possess strong potency and a range of therapeutic benefits that appear not to be shared by its decarboxylated form, cannabidiol (CBD). For example, cannabidiolic acid inhibits migration of the highly invasive MDA-MB-231 human breast cancer cells, via an apparent mechanism that may well apply to other cancer cells.

Additionally, the plant enzymes olivetolic acid geranyltransferase (EC number 2.5.1.102), cannabidiolic acid synthase (CBDA synthase, EC number 1.21.3.8) and tetrahydrocannabinolic acid synthase (THCA synthase, EC 1.21.3.7), responsible for the biosynthesis of CBGA/CBG, CBDA/CBD, and THCA/THC, resp., are known to only accept the carboxylate forms of the precursors in the pathway from olivetolic acid (or a Modified olivetolic acid) through cannabigerolic acid (CBGA) or cannabinerolic acid (CBNRA) or other prenylated 2,4-Dihydroxy-6-alkylbenzoic acid. With this in mind, it is an object of this invention to provide formulations of CBGA, olivetolic acid, or mixtures thereof that, when maintained at 4° C. for 6 months, exhibit retention of at least 50% of the CBDA in the carboxylated, non-degraded form, for use in production or bioproduction of cannabinoids.

It is an object of this invention to provide safe-for-consumption compositions comprising cannabidiolic acid (CBDA) that, when maintained at 23° C. for 6 months, exhibit retention of at least 50% of the CBDA in the carboxylated, non-degraded form.

It is another object of this invention to provide safe-for-consumption compositions comprising tetrahydocannabinolic acid (THCA) that, when maintained at 23° C. for 6 months, exhibit retention of at least 50% of the THCA in the carboxylated, non-degraded form.

It is another object of this invention to provide safe-for-consumption compositions comprising tetrahydocannabinolic acid (THCA) that, when maintained at 23° C. for 6 months, exhibit retention of at least 80% of the THCA in the carboxylated, non-degraded form.

It is another object of this invention to provide safe-for-consumption compositions comprising an active, acidic cannabinoid that, when maintained at 25° C. for 6 months, exhibit retention of at least 90% of said acidic cannabinoid in the carboxylated, non-degraded form.

It is another object of this invention to provide compositions comprising an Olivetolic acid derivative which, when maintained at 25° C. for 6 months, exhibit retention of at least 90% of said acidic cannabinoid in the carboxylated, non-degraded form.

It is a further object of this invention to provide safe-for-consumption compositions comprising an acidic cannabinoid selected from the group consisting of CBDA, THCA, CBGA, CBNRA (cannabinerolic acid), CBNA (cannabinolic acid), ajulemic acid, CBDVA, THCVA, and CBDVA that, when maintained at 23° C. for 6 months, exhibit retention of at least 50% of the CBDA in the carboxylated, non-degraded form.

It is another object of this invention to provide compositions comprising layered double-hydroxides intercalated with one or more (at least one) acidic cannabinoids wherein at least one of these cannabinoids displays significantly greater thermal stability than the pure cannabinoid; in particular, the half-life of the cannabinoid at 80° C. is over 8 hours, preferably over 20 hours, and most preferably over 60 hours.

It is another object of this invention to provide compositions comprising a 2,4-dihydroxy-6-alkylbenzoic acid that, when maintained at 25° C. for 6 months, exhibit retention of at least 50% of the 2,4-dihydroxy-6-alkylbenzoic acid in the carboxylated, non-degraded form, and functional for the release of one or more 2,4-dihydroxy-6-alkylbenzoic acids into a bioreactor or fermentation system comprising olivetolic acid geranyltransferase (EC number 2.5.1.102).

In some aspects, the invention provides an acidic cannabinoid-intercalated layered double-hydroxide (LDH) material in a form of an acidic cannabinoid-intercalated LDH particle, where the acidic cannabinoid-intercalated LDH particle has a general formula $M^{II}_{1-x}M^{III}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid. In certain aspects of the acidic cannabinoid-intercalated LDH material, $M^{II}$ is $Mg^{2+}$ or $Zn^{2+}$. In further aspects, $M^{III}$ is $Al^{3+}$. In additional aspects, $C^{1-}$ is cannabidiolic acid (CBDA), tetrahydrocannabinolic acid (THCA), cannabigerolic acid (CBGA), cannabinerolic acid (CBNRA), cannabinolic acid (CBNA), cannabidivarinic acid (CBDVA), tetrahydrocannabivarinic acid (THCVA) or cannabidivarinic acid (CBDVa). In some aspects, $C^{1-}$ is tetrahydrocannabinolate or cannabidiolate. In other aspects, the acidic cannabinoid-intercalated LDH material is in a form of a free-flowing powder. In some aspects, x is from 0.14 to 0.33. In other aspects, x is from 0.25 to 0.33. In other aspects, m is from 0 to 0.25.

The invention also provides a pharmaceutical composition, comprising an acidic cannabinoid-intercalated layered double-hydroxide (LDH) material in a form of an acidic cannabinoid-intercalated LDH particle, where the acidic cannabinoid-intercalated LDH particle has a general formula $M^{II}_{1-x}M^{III}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid; and a physiologically acceptable carrier. In some aspects, the pharmaceutical composition is a dispensable aerosolized formulation suitable for administration to a human or a non-human subject. In some aspects, the carrier is a gas propellant. In additional aspects, the gas propellant is selected from the group consisting of a hydrofluorocarbon, an alkane, and air. In further aspects, the pharmaceutical composition is formulated for topical administration to a human or a non-human subject. In some aspects, the pharmaceutical composition is formulated as eye drops. In other aspects, the pharmaceutical composition is formulated as a cream, lotion or ointment. In additional aspects, the pharmaceutical composition is incorporated in a cosmetic. In yet further aspects, the pharmaceutical composition is formulated for transdermal administration to a human or a non-human subject. In some aspects, the pharmaceutical composition is formulated for oral administration to a human or non-human subject. In certain aspects, the pharmaceutical composition is formulated for administration by injection to a human or non-human subject. In other aspects, the pharmaceutical composition is formulated for otic administration to a human or non-human subject. In other aspects, the pharmaceutical composition is formulated for rectal administration to a human or non-human subject. In additional asepcts, the pharmaceutical composition is formulated for vaginal administration to a human or non-human subject.

The invention also provides a wearable garment comprising an acidic cannabinoid-intercalated layered double-hydroxide (LDH) material in a form of an acidic cannabinoid-intercalated LDH particle, where the acidic cannabinoid-intercalated LDH particle has a general formula $M^{II}_{1-x}M^{III}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid.

The invention also provides a method of treating a disease or condition involving 5-HT1A receptors in a subject in need thereof, comprising administering to the subject a therapeutically effective amount of an acidic cannabinoid-intercalated layered double-hydroxide (LDH) material in a form of an acidic cannabinoid-intercalated LDH particle, where the acidic cannabinoid-intercalated LDH particle has a general formula $M^{II}_{1-x}M^{III}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid, and aspects thereof as described above. In some aspects, the disease or condition is selected from the group consisting of post-traumatic stress disorder (PTSD), anorexia, depression, drug addiction, social phobia, schizophrenia, schizoaffective disorder, bipolar disease and psychosis.

The invention also provides a method of treating epilepsy in a subject in need thereof, comprising administering to the subject a therapeutically effective amount of an acidic cannabinoid-intercalated layered double-hydroxide (LDH) material in a form of an acidic cannabinoid-intercalated LDH particle, where the acidic cannabinoid-intercalated LDH particle has a general formula $M^{III}_{1-x}M^{II}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid, and aspects thereof as described above. In certain aspects, the step of administering is performed topically via the wearing of a garment impregnated with the acidic cannabinoid-intercalated LDH material.

The invention also provides a method of treating pain and/or nausea in a subject in need thereof, comprising administering to the subject a therapeutically effective amount of an acidic cannabinoid-intercalated LDH particle, where the acidic cannabinoid-intercalated LDH particle has a general formula $M^{II}_{1-x}M^{III}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid, and aspects thereof as described above. In certain aspects, the subject is a cancer patient who is receiving chemotherapy.

The invention also provides an aerosol metered dose inhaler containing an acidic cannabinoid-intercalated LDH particle, where the acidic cannabinoid-intercalated LDH particle has a general formula $M^{II}_{1-x}M^{III}_{x}(OH)_2(C^{1-})_x \cdot mH_2O$, wherein x is from 0.1 to 0.4; m is from 0 to 0.50; $M^{II}$ is chosen from the group consisting of $Mg^{2+}$, $Co^{2+}$, $Ni^{2+}$, $Cu^{2+}$, $Zn^{2+}$, and $Ca^{2+}$; $M^{III}$ is chosen from the group consisting of $Al^{3+}$, $Fe^{3+}$, $Cr^{3+}$, $Ga^{3+}$ and $Bi^{3+}$; and $C^{1-}$ is a deprotonated acidic cannabinoid, and aspects thereof as described above, in a free-flowing powder form.

The invention also provides a particulate material, comprising: an olivetolic acid derivative intercalated in a layered double-hydroxide (LDH) particle, wherein the particulate material has a general formula defined by $M^{II}_{1-x}M^{III}_{x}(OH)_2(C^{1-})_x \cdot mH_2O$, where $M^{II}$ is chosen from the group consisting of $Mg^{2+}$, $Co^{2+}$, $Ni^{2+}$, $Cu^{2+}$, $Zn^{2+}$, and $Ca^{2+}$, $M^{III}$ is chosen from the group consisting of $Al^{3+}$, $Fe^{3+}$, $Cr^{3+}$, $Ga^{3+}$ and $Bi^{3+}$, $C^{1-}$ is the olivetolic acid derivative, x ranges 0.1 to 0.4, and m ranges from 0 to 0.5. In some aspects, x ranges from 0.14 to 0.33. In other aspects, x ranges from 0.25 to 0.33. In additional aspects, m ranges from 0 to 0.25. In further aspects, the olivetolic acid derivative is an acidic cannabinoid. In some aspects, the acidic cannabinoid is a phytocannabinoid. In further aspects, the acidic cannabinoid is selected from the group consisting of is cannabidiolic acid (CBDA), tetrahydrocannabinolic acid (THCA), cannabigerolic acid (CBGA), cannabinerolic acid (CBNRA), cannabinolic acid (CBNA), cannabidivarinic acid (CBDVA), tetrahydrocannabivarinic acid (THCVA) or cannabidivarinic acid (CBDVa). In certain aspects, the particulate material, when maintained at 23° C. for 6 months, retains at least 50% of the cannabinoid in a carboxylated, non-degraded form. In some aspects, the cannabinoid is CBDA. In other aspects, the cannabinoid is THCA. In additional aspects, the cannabinoid is CBGA. In some aspects, the cannabinoid is CBNRA. In other aspects, the cannabinoid is CBNA. In additional aspects, the cannabinoid is CBDVa. In some aspects, the particulate material, when maintained at 25° C. for 6 months, exhibits retention of at least 90% of the olivetolic acid derivative in a carboxylated, non-degraded form. In further aspects, the olivetolic acid derivative is CBDA. In further aspects, the olivetolic acid derivative is THCA. In other aspects, the olivetolic acid derivative is CBGA. In yet other aspects, the olivetolic acid derivative is CBNRA. In yet additional aspects, the olivetolic acid derivative is CBNA. In other aspects, the olivetolic acid derivative is CBDVa. In additional aspects, the olivetolic acid derivative is an amorfrutin. In further aspects, the amorfrutin is selected from the group consisting of 2-hydroxy-4-methoxy-3-(3-methyl-2-buten-1-yl)-6-(2-phenylethyl)-benzoic acid and 3-[(2E)-3,7-dimethyl-2,6-octadien-1-yl]-2-hydroxy-4-methoxy-6-(2-phenylethyl)-benzoic acid.

The invention also provides a composition comprising an olivetolic acid derivative exhibiting intermittent or flickering chemisorption and physiosorption to one or metal atoms selected from the group consisting of Mg, Co, Ni, Cu, Zn, Ca, Al, Fe, Cr, Ga, and Bi, and which, when maintained at 25° C. for 6 months, exhibits retention of at least 90% of said Olivetolic acid derivative in the carboxylated, non-degraded form. In some aspects, the olivetolic acid derivative is CBDA. In other aspects, the olivetolic acid derivative is THCA. In additional aspects, the olivetolic acid derivative is CBGA. In yet further aspects, the olivetolic acid derivative is CBNRA. In other aspects, the olivetolic acid derivative is CBNA. In yet other aspects, the olivetolic acid derivative is CBDVA.

The invention also provides a powder comprising a plurality of particulate materials or composition, wherein said particulate materials have a diameter or a largest dimension ranging from 0.1 to 100 microns. In some aspects, the diameter or the largest dimension ranges from 0.1 to 50 microns. In other aspects, the diameter or the largest dimension ranges from 0.1 to 10 microns.

The invention also provides a method of producing a particulate material, composition, or powder described in any of the preceding paragraphs, comprising intercalating an olivetolic acid derivative into a layered double-hydroxide (LDH) particle or particles.

The invention also provides a formulation for topical application to a subject, comprising: a plurality of particulate materials, wherein said particulate materials have a diameter or largest dimension ranging from 0.1 to 100 microns; and a pharmaceutically acceptable carrier. In some aspects, the pharmaceutically acceptable carrier is an aqueous liquid. In other aspects, the pharmaceutically acceptable carrier is a polar solvent. In additional aspects, the pharmaceutically acceptable carrier is a cream. In yet further aspects, the pharmaceutically acceptable carrier is a lotion.

DETAILED DESCRIPTION OF THE INVENTION

Definitions

Figure 1:
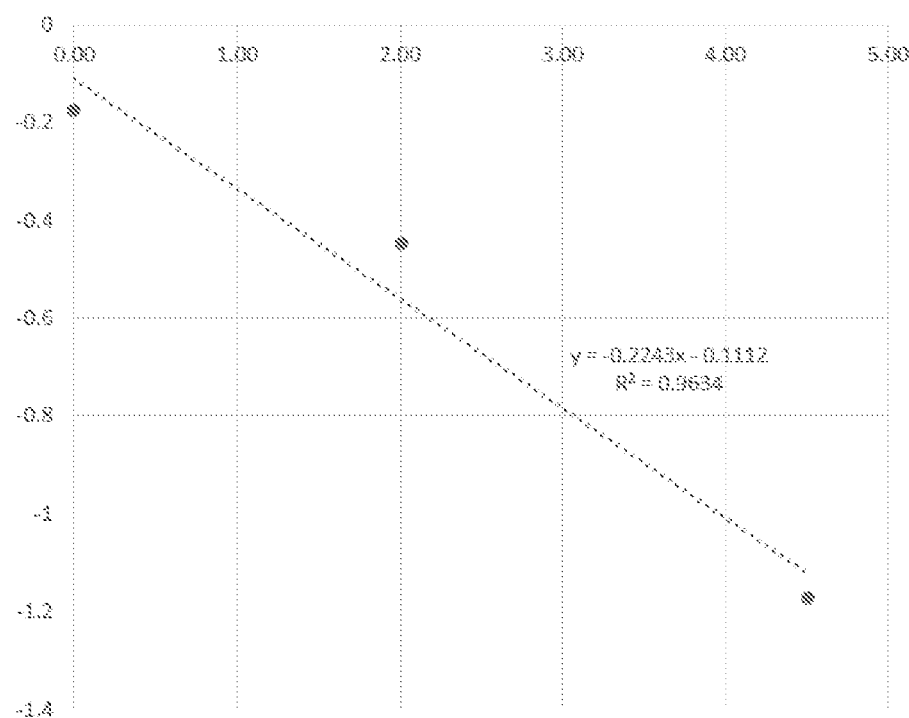
FIG. 1. A plot of Ln P=Ln {[CBDA]/([CBDA]+[CBD])} as a function of time in hours at 80° C., for samples of "Alleviate X" CBDA-rich hemp extract.

"Phytocannabinoid": Phytocannabinoids are, by definition, cannabinoids well known to be biosynthesized in plants of the *Cannabis* genus (Cannabaceae family), namely *C. sativa, C. indica, C. rudaleris* and crossbreeds thereof, and are all derived from olivetolic acid or a closely related alkylresorcylic acid.

"CBDA": cannabidiolic acid; CAS no. 1244-58-2; 3-p-mentha-1,8-dien-3-yl-6-pentyl-beta-resorcylic acid.

"THCA": tetrahydrocannabinolic acid; CAS no. 23978-85-0; (6aR,10aR)-1-hydroxy-6,6,9-trimethyl-3-pentyl-6a,7,8,10a-tetrahydrobenzo[c]chromene-2-carboxylic acid.

"CBGA": cannabigerolic acid (CAS no. 25555-57-1), 3-[(2E)-3,7-dimethylocta-2,6-dienyl]-2,4-dihydroxy-6-pentylbenzoic acid.

"CBNA": cannabinolic acid (CAS no. 2808-39-1).

"CBNRA": cannabinerolic acid, 3-[(2Z)-3,7-dimethylocta-2,6-dienyl]-2,4-dihydroxy-6-pentylbenzoic acid.

"CBCA": cannabichromenic acid (CAS no. 185505-15-1).

"THCVA", "CBDVA", etc.: Insertion of the letter "V" in the abbreviated cannabinoid notation indicates that the pentyl chain is replaced by a propyl chain; for example, CBDVA is 3-p-mentha-1,8-dien-3-yl-6-propyl-beta-resorcylic acid; CBGVA is cannabigerovarinic acid; THCVA is tetrahydrocannabivarinic Acid THCVA, CAS Number: 39986-26-0), etc.

In these definitions, it should be noted that certain of these compounds have isomers, such as the famous example of Δ9-THCA and Δ8-THCA, and for the purposes of this disclosure the Δ9- and Δ8-cannabinoid will be treated both as simple "THCA", as it is highly unlikely that this small shift, at its distance from the labile carboxyl group, would make a difference in intercalation or in stability of the intercalated cannabinoid. Certainly differences in therapeutic effect(s) can occur with this simple change, but if one of these isomers is suitable for LDH intercalation as per the invention, then almost certainly the other will be as well.

"Olivetolic acid" (CAS no. 491-72-5): the IUPAC preferred name is 2,4-Dihydroxy-6-pentylbenzoic acid; it can also be called pentylresorcinolic acid.

"Modified olivetolic acid": in this disclosure, only a 2,4-Dihydroxy-6-alkylbenzoic acid will be termed a "modified olivetolic acid"; that is, only the pentyl chain length and branching can be changed from n-pentyl (no branching, 5 carbons) to such compounds as 2,4-Dihydroxy-6-propylbenzoic acid (3 carbons, no branching), etc. Thus, "modified olivetolic acid" will be synonymous with "2,4-Dihydroxy-6-alkylbenzoic acid", but not with "olivetolic acid derivative" which is a much broader class that includes the acidic cannabinoids.

"Olivetolic acid derivative": in this disclosure, "olivetolic acid derivative" will these compounds and only these compounds:

"Modified olivetolic acids" as defined above; and

Compounds that retain a "Modified olivetolic acid", that is, a 2,4-Dihydroxy-6-alkylbenzoic acid group, in some cases with substitution of the hydrogen in one of the OH [hydroxyl] bonds to form an ether bond, as in THCA and CBCA), in their molecular structure; these include the phytocannabinoids, and certain synthetic cannabinoids, though not the synthetic cannabinoid ajulemic acid because the carboxylic acid group in ajulemic acid is not attached to the alkylresorcinol group.

In particular, CBDA, TCHA, CBGA, CBNRA, CBNA, CBCA, and each of these with the "V" or "varin" designation (propyl side chain), as well as olivetolic acid and 2,4-dihydroxy-6-alkylbenzoic acids, are all Olivetolic acid derivatives; this is the case whether the carboxyl group is protonated (carboxylic acids) or deprotonated as in a pharmaceutically acceptable salt (e.g. carboxylates), and herein the term "Olivetolate derivative" means an Olivetolic acid derivative in which the carboxyl group is de-protonated, such as in a salt or other ionic form; that is, an Olivetolate derivative is the conjugate base of the corresponding Olivetolic acid derivative. "Half-life", always cited at a specific temperature, is the average time it takes for 50% of the active to degrade at that temperature and humidity to a degradant (a decarboxylated cannabinoid or quinone degradant, in most embodiments herein), also phrased as 50% retention of intact, unchanged active. The IUPAC definition is in agreement with this and is as follows: For a given reaction the half life t½ of a reactant is the time required for its concentration to reach a value that is the arithmetic mean of its initial and final (equilibrium) values.

"Shelf-life": Regulatory agencies in developed counties typically conform to the FDA guidances for Real-Time Stability, which depend to some extent on the drug product format (sterile vs non-sterile, enclosed vial, multiple use vs single-use, etc.), but are typified by the following statement: "The target stability is the next to last tested point that was within +/−10% of time zero." One with skill in the art will recognize that this is a valid general rule of thumb, and that claiming a shelf-life longer than that 10%-loss point will likely be very problematic from a regulatory perspective. In the event that a degradant is particularly toxic, the permitted degradation may be even less than 10%. For a formulation with a complicated release mechanism, Real-Time Release should also be studied for a sample at the end of the shelf-life (i.e., near or at the expiration date).

"Physisorption": The IUPAC definition of physisorption is as follows: Adsorption in which the forces involved are intermolecular forces (van der Waals forces) of the same kind as those responsible for the imperfection of real gases and the condensation vapours, and which do not involve a significant change in the electronic orbital patterns of the species involved.

"Chemisorption": The IUPAC definition of chemisorption is as follows: Adsorption which results from chemical bond formation (strong interaction) between the adsorbent and the adsorbate in a monolayer on the surface.

"LOQ": Limit of Quantification, in the exact sense known to one skilled in the art of high-performance liquid chromatography (HPLC).

"Non-covalent" has a specific meaning in the context of this invention, as it means an interaction or bond (herein, between cannabinoid and layered double-hydroxide) that is not a long-lived covalent bond, and in particular, does not remain covalent continuously for longer than one hour under ambient or near-ambient conditions; thus, a bond that "flickers" between covalent and simple physisorption (which is not covalent) on a timescale faster than one hour is a non-covalent bond, in the context of this invention; when exposed to a solvent or a delivery site in a mammal, the bond will eventually break and the released cannabinoid will be in its native state and thus not a New Chemical Entity. "Flowable powder": Qualitatively, a powder is a "flowable powder" in this disclosure only if it displays sufficient flow in a specific piece of equipment or packaging i.e. capsule filler, blender, or feeder hopper, etc., at the conditions (temperature and humidity) reasonably representative of those encountered in manufacture; USP 35 General Information/ (1174) Powder Flow describes the standardized procedure for measuring the angle of repose (essentially, the angle of tilt at which flow continues), and quantitatively in this patent disclosure, a powder is a "flowable powder" if the angle of repose is less than 45 degrees, and preferably less than 35 degrees. A "flowable powder" may also be referred to as a "free-flowing powder" herein.

"Sustained release", "controlled release", "extended release", "long-acting", "gradual release", "modified release", "prolonged action", and "slow release": A dosage form is "sustained release" if it is designed to release the drug contained therein at a continuous and controlled rate for a longer period of time than can normally be achieved with its conventional, nonsustained counterpart in the same route of administration.

"Aerosol": Aerosols are dosage forms that are packaged under pressure and contain therapeutic agent(s) and a propellant that are released upon actuation of an appropriate valve system. Aerosols are intended for topical application to the skin as well as local application into the nose (nasal aerosols), mouth (lingual aerosols), or lungs (inhalation aerosols). These products may be fitted with valves enabling either continuous or metered-dose delivery.

"Films": Films are thin sheets that are placed in the oral cavity. They contain one or more layers. A layer may or may not contain a drug substance.

"Gels": Gels are semisolid systems consisting either of suspensions of small inorganic particles or of organic molecules interpenetrated by a liquid.

"Transdermal": Transdermal delivery systems are self-contained dosage forms that, when applied to intact skin, are designed to deliver the active(s) through the skin to the systemic circulation.

"Polar solvent": Polar solvent is a type of solvent that has large partial charges or dipole moments, generally with dielectric constant greater than or equal to about 40, and is miscible with water. The bonds between the atoms have very different but measurable electronegativities. A polar solvent can dissolve ions and other polar compounds. Polar solvents—not including toxic or reactive compounds—include water, formamide, N-methylformamide, dimethylformamide (DMF), dimelthylsulfoxide (DMSO), N-methylacetamide, dimethyacetamide, N-methylpyrrolidone (NMP), glycerol, propylene carbonate, and mixtures thereof.

"Amorfrutins": Any of a class of isoprenoid-substituted benzoic acid derivatives found in *Amorpha fruticosa*. Amofrutin A, which is 2-hydroxy-4-methoxy-3-(3-methyl-2-buten-1-yl)-6-(2-phenylethyl)-benzoic acid, and amorfrutin B, which is 3-[(2E)-3,7-dimethyl-2,6-octadien-1-yl]-2-hydroxy-4-methoxy-6-(2-phenylethyl)-benzoic acid, are currently the two most prevalent derivatives, and are known to have potent activities upon binding to PPARγ, and in particular more potency than their decarboxylated analogs.

In this disclosure, various shorthand notations for the deprotonated acidic cannabinoids, amorfrutins, and other olivetolic acid derivatives will be used interchangeably, exemplified now for the case of CBDA. The longer name for deprotonated CBDA is cannabidiolate (noting that a cationic counterion is generally present), and for brevity this disclosure uses the following notations for this anion: $CBDA^-$; $CBDA^{1-}$, $C^{1-}$ (in the LDH chemistry description, where "C" is short for "cannabinoid" or other olivetolic acid derivative), or in some cases LDH-CBDA will be used, where clearly the CBDA is present almost entirely in deprotonated (anionic) form and the LDH is of course net cationic. One skilled in the art will recognize that these represent the so-called conjugate base of the acidic compound.

DETAILED DESCRIPTION OF THE INVENTION

Acidic cannabinoids have 3 main physicochemical features of central importance in this disclosure: a) a 2,4-Dihydroxy-6-alkylbenzoic acid group; b) the canonical cannabinoid structure related to cannabigerolic acid (CBGA), derived from prenylation of olivetolate; and c) a decarboxylation tendency due to OH-substitutions at the 4 (para) and, particularly, the 2 (ortho) positions of the benzoic acid backbone of olivetolic acid. Cannabidiolic acid (CBDA) is known to have powerful therapeutic effects in some indications and conditions, including antiemetic and antiepileptic effects at doses of micrograms per mL (mcg/mL) in mice and clinical models (see, e.g., WO 2017/025712). The recent failure of a clinical trial using the extremely high-purity CBD drug formulation known as Epidiolex® in acute treatment of anxiety, utilizing CBD doses of up to 900 mg and reporting essentially zero effect (see NCT02902081), is reasoned in the present disclosure to be due to the removal of a much more powerful cannabinoid during the rigorous purification of Epidiolex®; this purification goes far beyond that typical in the CBD supplements market. Indeed, it is consistent with the teachings of this patent that many of the therapeutic effects of hemp-derived products are due not to cannabidiol (CBD), but rather to CBDA—often viewed as an "impurity"—and while these effects may require the assistance of other cannabinoids such as THC, CBD, or tetrahydrocannabinolic acid (THCA), CBDA is the most potent of all these for the indications above. This conclusion, and therefore to some extent the very basis of this patent disclosure, would be considered very surprising to nearly all those working currently in the "CBD" and "hemp oil" industries, who have developed myriad methods for removing and discarding CBDA from hemp oils in order to claim high purity CBD products; see, e.g., U.S. Patent App. Application #20180016216.

Olivetolic acid, which itself has potential importance for feed stocks in the production of cannabinoids by techniques such as cell culture [see, e.g., U.S. Pat. No. 10,704,066] and bioreactor-based methods, possesses hydroxyl (OH) groups at the 2- and 4-positions, and can be viewed as a 3-position alkylated derivative of beta-resorcylic acid. Beta-resorcylic acid has in common with salicylic acid a tendency to decarboxylate over time scales of weeks at ambient temperature, and traces of acid or heavy metals (esp. copper ions) can dramatically increase this rate. The facts that cannabis plants are strongly hyperaccumulatory for many heavy metals, and that cannabis extracts generally contain at least small amounts of formic acid, amplify this problem. Methylation of salicylic acid at the facile carboxyl group greatly increases the stability. Similarly, methylation of cannabidiolic acid, to form methyl cannabidiolate, is taught in U.S. Patent App. #20190091144. However, from essentially every perspective this creates a new compound, different from CBDA in myriad respects: it is not a natural product (phytochemical, in the instant disclosure), is has different pharmacokinetics and likely pharmacodynamics as well, is already considered a drug by the FDA, and affects the blood-brain barrier.

When Epidiolex® was recognized as a drug by the FDA, then current laws dictate that the active compound (CBD, clearly; see the above) should no longer be available as an OTC supplement. At the time of this writing, CBDA is not recognized by the FDA as a drug. Therefore, a stable and safe formulation of CBDA, substantially free from CBD, and free from covalent modifications of the CBDA, is highly desirable.

Accelerated thermal stability studies of acidic cannabinoids, CBDA and THCA, as reviewed herein are in substantial agreement that the half-lives of these two compounds are only about 4 weeks at 40° C. and about 12 weeks at 30° C., and this is true for the neat substances as well as solutions, with many solutions, including hemp oil itself. This means that half-lives of these compounds in any current formulation cannot be reliably greater than about 4 months unless a cold-chain is enforced. Furthermore, for pharmaceutical or more heavily regulated applications, it is not the half-life (50% degradation) but rather the point of 10% degradation that must be controlled, and without a cold-chain this could not be reliably maintained for much more than 1 month, with any prior art formulation of CBDA or THCA. And this does not even account for decarboxylation that inevitably occurs for these compounds during the cannabinoid extraction and preparation of the formulation, where for example it is known that even short contact with steel can rapidly decarboxylate these compounds.

In addition to major stability problems and limitations, acidic cannabinoids are also notoriously sticky materials, typically with extremely low solubilities in water, issues that cause problems in formulating and administering these compounds; the carboxyl groups of acidic cannabinoids in particular can contribute strongly to adhesiveness. This is further complicated by the low bioavailability of cannabinoids in simple oral formulations lacking slow release, and instability with heating limits or precludes common "delivery" methods such as smoking and vaping. Objectionable organoleptic and safety issues associated with neat or solution formulations of acidic cannabinoids include objectionable taste, TRPV1 activation creating a "hot" sensation in the mouth, objectionable odor, and a tendency toward contamination by heavy metals due to the hyperaccumulatory nature of the *cannabis* plant and carboxylated compounds therein. The most commonly used carrier liquids for solubilizing cannabinoids, namely medium-chain triglycerides (MCT oil) and related oils, themselves suffer from instabilities such as oxidation and de- or trans-esterification (e.g., substitution of an acidic cannabinoid for an acyl chain of the triglyceride) at ambient temperatures over time. Also, creation of free fatty acids from de-esterification of one or more acyl chains of MCT oil will lower pH over time and therefore directly reduce the stability of the acid-labile cannabinoids of the invention.

The present invention is able to overcome a number of the inherent instability, formulation difficulties, and objectionable organoleptic properties of acidic cannabinoids. Surprisingly, the inventor has found that certain compositions comprising an intercalated anionic clay or clay-like material with the general formula given by $M^{II}_{1-x}M^{III}_x(OH)_2(C^{1-})_x \cdot mH_2O$, where $M^{II}$ is chosen from the group consisting of $Mg^{2+}$, $Co^{2+}$, $Ni^{2+}$, $Cu^{2+}$, $Zn^{2+}$, and $Ca^{2+}$, $M^{III}$ is chosen from the group consisting of $Al^{3+}$, $Fe^{3+}$, $Cr^{3+}$, $Ga^{3+}$ and $Bi^{3+}$, $C^{1-}$ is a deprotonated acidic cannabinoid, x lies preferably in the range 0.25-0.33, and m is less than about 0.5, exhibit strongly enhanced stability against decarboxylation and other degradation reactions, ease of formulation and delivery due to the dry powder format of the intercalate, and diminishment of objectionable tastes and odors known to be associated with many, if not most, cannabinoids.

It should be noted that the protective matrix provided by the LDH of the present invention may in some embodiments offer significant reductions of the organoleptic issues with acidic cannabinoids (bad taste, bad odor, stickiness, etc.), as well as tunable release characteristics, but not necessarily with an accompanying improvement in the decarboxylation issue. Without wishing to be bound by theory, significant improvement in stability against decarboxylation requires an additional feature, namely a favorable bond type and energy between the cannabinoid and the LDH, something which is discussed in more detail below, where a method for measuring and deducing the bond type and energy are also provided.

Materials and Methods.

The intercalated materials of the present invention can be produced via several simple and inexpensive routes, one of which (the "co-precipitation" method) is explicitly reported in the Example 1 below. In another route, hydrotalcite is first calcined, for example by heating in a muffle furnace at 450° C. for several hours. This double oxyhydroxy (usually referred to as a "mixed oxide") is capable of regenerating the original LDH structure through what is known as the "memory effect"; that is, the mixed oxide created during calcination apparently retains enough structural aspects of the original hydrotalcite that it is predisposed to regenerating it given the right conditions. This reaction would be done in the presence of the olivetolate derivative in the present invention, at or near ambient temperature (i.e., not requiring high temperatures that could cause decarboxylation). While this is typically done in an aqueous medium, the problems caused by extremely low aqueous solubility of cannabinoids and inadvertent intercalation of polar solvents, make this approach challenging. Calcined hydrotalcite is available commercially, saving one the step of calcination, and potentially reducing costs.

If the original portion of hydrotalcite used contains an amount, call it X moles, of intercalated acetate ions, then one preferably should use a slight excess over X moles of anionic surfactant (or of total anionic groups more generally, because the surfactant could be multivalent), or if the olivetolate derivative is intercalated without the prior intercalation of a surfactant, an excess of the derivative is also favorable. Naturally, since the laws of mass action govern the equilibrium between the mixed oxide and the surfactant, as well as the competition between surfactant anion and other anions present such as carbonate in particular, it is preferred in most cases that the concentrations of the desired anions be relatively high. In academic studies using concentrated systems, say 10% surfactant in water, with a stoichiometric amount of mixed oxide, the reaction is usually run for at least 8 hours, though much shorter durations are possible once conditions for industrial production are optimized. It is preferable that organic anion (surfactant, or olivetolate derivative) concentrations in the reaction step be at least 0.1%, and more preferably 1% or greater, except in cases where the product is manufactured in situ, which is discussed next.

More direct, and potentially cheaper, methods of preparing organic-intercalated LDHs have been described in the literature and are adapted in this disclosure to the sensitive olivetolate derivatives of this invention. The co-precipitation in Jobbagy and Regazzoni (2004) and the homogeneous precipitation method in Iyi et al. (2009) are preferred methods in the practice of the present invention. The Examples section below describes a simple co-precipitation production method that is readily scalable. Water-soluble salts of the zinc, magnesium, aluminum, or other di- or tri-valent metal ions are dissolved in decarbonated water, with the nitrate salts being particularly favorable as nitrate ions are relatively easily displaced by organic ions, e.g., cannabidiolate ion ($CBDA^{1-}$). In the present invention, it may be necessary to raise the pH of this solution closer to neutral, so as to avoid acid-catalyzed decarboxylation of the olivetolate moiety. Then, under strong stirring, minimal (or diverted) lighting, inert gas, and using decarboxylated water in all steps including washing, a solvent containing dissolved CBDA (or other olivetolic acid derivative) is alternately exposed to additions of the metal nitrates solution and a strong base, usually NaOH in decarboxylated water, in order to maintain a pH above 7, and preferably between about 8 and 11, and more preferably between about 8.5 and 10.5. It will be noted that most reported co-precipitation preparations of intercalated LDHs were focused on intercalating organic anions that are soluble in water (as salt forms). In the present invention, most of the olivetolate derivatives of interest have very low solubility in water, far less than 1 milligram per milliliter in general, and as low as an estimated 3 microgram per liter for CBDA. Such low solubilities mean that if an organic solvent is not used, then huge volumes of water would be required in order to solubilize an effective amount of active, complicating manufacture, greatly slowing reaction rates, and requiring control of carbonates in the water.

In the present invention, these obstacles and others are circumvented by using a two-phase system, in which the olivetolic acid derivative is introduced via a non-polar solvent or solvent mixture, while the metal salts are of course introduced via aqueous solution or using a polar (co-)solvent such as glycerol. Strong mixing is therefore required, to obtain sufficient contact between reactants and intercalating compounds. While another possible approach is to use a water-miscible solvent for the olivetolate, it can be difficult to find a workable one-phase solvent mixture that can simultaneously solubilize the metal salts and an anionic cannabinoid, particularly since some prominent polar or amphiphilic solvents, like the formamides, are known to intercalate into LDHs. It is known as well that many polar solvents can accelerate the decomposition of beta-hydroxy benzoic acid derivatives such as salicylic acid, such solvents including alcohols (particularly glycols), pyridine, nitrobenzene, etc. Also, the use of surfactants is generally problematic since: a) many surfactants can compete with an anionic cannabinoid for intercalation; and b) subsequent work-up to extract the invention from such a reaction mixture could be complicated by the surfactant due to the formation of durable emulsions. Following the reaction period, mild centrifugation and/or filtration is then used to remove solvents, and to aid in washing the intercalated LDH material with both (decarboxylated) water and (sparged) solvents; it must be stressed that washing post-reaction is a critical step since unremoved anions, such as nitrate ions when metal nitrates are used, can exchange with the desired anion, expelling the cannabinoid from the LDH and even solubilizing it if a non-polar solvent remains. Lyophilization (freeze-drying) provides another means to remove water, but of course water-solubles such as sodium nitrate will be left behind, again posing potential problems. If the reaction is carried out as just described, and as demonstrated below, and the intercalated LDH properly washed, then the non-volatile organic anions of the invention, such as cannabidiolate ($CBDA^{1-}$), will be effectively entrapped in the LDH.

The liquid used for solubilizing the cannabinoid in, e.g., the 2-phase method described above, is preferably selected from the group consisting of medium-chain triglyceride (MCT) or other coconut oil extract, anisole, pinene, dibutyl ether, xylene, allylbenzene, trichloroethylene (stabilized), and mixtures thereof. Preferably the dielectric constant of the solvent or solvent mix is close to 4, most preferably in the range of 2.5-4.5.

Exposure to carbon dioxide in air or in a formulation can potentially displace the desired organic anion from the interior of the LDH particles to the surface, where it may not be as well protected against decarboxylation and oxidation. Fortunately, the ultralow solubility of cannabinoids in water means that in the absence of surfactant or a solubilizing liquid, the acidic cannabinoid has nowhere to migrate that offers a more favorable milieu than the LDH and has far too low a vapor pressure to evaporate at a non-trivial rate (the vapor pressure of CBD, for example, at ambient temperature is an estimated $3\times10^{-6}$ Pa). Experimentally, this was seen in the present work, where CBDA was found to degrade when the temperature rose during the centrifuge step of the cyclohexane wash (due to a centrifuge malfunction in its refrigeration); since solvent was still present (cyclohexane), the formed LDH was not capable of fully protecting the CBDA against de-intercalation followed by degradation, while similar temperature exposure of the final washed and dried intercalate induced negligible degradation over far longer time periods (days vs minutes). Thus, from a production perspective, it must be borne in mind that the cannabinoid is not "safe" until any organic solvent(s) for the cannabinoid are removed. Similarly, even a short migration out of the LDH into, e.g., a solvent or surfactant-rich aqueous medium, can result in rapid oxidation of the cannabinoid if oxygen is present (e.g., dissolved air, entrained air, etc.), even while oxidation of intercalated cannabinoid is shown in Example 5 below to be strongly retarded even in the presence of strong oxidizers (weeks vs seconds). Due to the potential for $CO_2$ and/or oxygen to induce degradation (albeit very slow degradation) even for the dry intercalate powder, for pharmaceutical applications it is recommended that the intercalated LDH or formulation thereof be packaged in an air-tight container, preferably filled with inert gas.

Substantial removal of active (acidic cannabinoid) from the outer surface of particles may be possible through the use of anions of high molecular weight, which can displace surface-adsorbed active but are too large to significantly enter the LDH. One example of such an anion would be polyacrylate (i.e., polyacrylic acid in de-protonated, or salt, form), or more preferably, a copolymer of polyacrylate with a neutral monomer (e.g., hydroxyethylmethacrylate). Therefore, in some applications involving a coating, it may be possible to effect both surface-removal of the active and particle coating with a bioadhesive polymer, in a single step.

In the manufacturing setting, particle size control can be obtained by a number of methods with their relative advantages and disadvantages. In some processes, relatively large (supermicron) particle aggregates of intercalated LDH are synthesized, and these are then broken down into finer and finer particles by either a dispersion-based process such as microfluidization (high-speed homogenization), ultrasonication, or by the hydrothermal treatment described by Xu et al. [J. Phys. Chem. B (2006) 110:16923]. In Xu's hydrothermal method, aggregated LDH created under fast nucleation conditions, and thus with a small primary crystallite size, is first washed with water to remove unreacted components, and the washed powder is then dispersed in water by heating for 2-4 hours. Shorter than this is insufficient, and longer than 4 hours results in a gradual increase in particle size. The mechanism is believed to be the removal of amorphous regions that bridge together primary crystallites, after which the submicron particles can be stabilized in dispersion by, e.g., a positive zeta potential. In Xu's publication, the interlayer anions were not of the sort in the embodiments of the current invention; rather than being anionic surfactants or olivetolate derivatives, they were low-MW anionic groups such as nitrate, carbonate, chloride, acetate, etc.

Returning to production means, the raw dispersion from the intercalation step can also be micronized using powder milling methods. Milling to nanocrystal size (less than about 400 nm) is now a well-developed technique for which a variety of milling media (abrasive particles) are available, including organic media. The current inventor has described and used such milling methods to create an FDA-approved nanocrystal formulation of sodium dantrolene that is acceptable for intravenous injection, where particle sizes above a few microns is unacceptable if not deadly. See U.S. Pat. No. 7,758,890 and others of that lineage.

Variations on the synthesis route are increasingly available, such as the 2009 method of Iyi et al. [J. Coll. Int. Sci. (2009) 340:67]. In that method, the synthesis of a surfactant-intercalated LDH proceeds in a single step, with an ammonia-releasing reagent such as hexamethylenetriamine required.

Water is not the only choice for the continuous phase, or "carrier", of the surfactant-intercalated LDH dispersion. Dispersions of intercalated LDH particles, including some which are translucent, are readily obtained using organic solvents. Other matrices for the intercalates are discussed elsewhere herein.

Embedding the particles into a solid or solid-like matrix such as a polymer-preferably one that is readily soluble in water or a body fluid, such as stomach acid or saliva—can be beneficial for ease or transport of the product, permitting use as a solid or coarse powder while minimizing the losses and health hazards associated with ultrafine powder, and providing a protective matrix for the LDH particles providing stability, desired bioadhesion characteristics, and desired release characteristics. Especially, embedding the particles in a material with low oxygen permeability, preferably less than $10^{-15}$ $cm^3$ (STP)cm/($cm^2$ see Pa), can prevent oxidation of acidic cannabinoids to quinones, CBN, and other oxidative degradants. Methods well known in the art for embedding powdered additives into polymers can be applied to the dried powder. Alternatively, without requiring expensive drying steps, monomer, crosslinker, and/or functionalized (generally crosslinkable) polymer can be added to a dispersion of the particles and subsequently crosslinked, to form a hydrogel or organogel in which the intercalated-LDH particles are embedded. With a high enough crosslink density, such that the average distance between crosslinks is smaller than the average particle size, the particles will be immobilized in the gel. A lower crosslink density could be used to allow for particle egress from the gel via diffusion, although the gel would tend to lose physical integrity in such a case were the loading too high. Cost-effective, water-soluble polymers of low environmental impact that could be useful for embedding the LDH particles include both synthetic polymers such as acrylates, acrylamides, PVP, polyethylene glycol (of MW larger than about 800), and natural polymers such as acacia, gum tragacanth, xanthan, karaya and combinations thereof such as acacia/tragacanth mixtures. Certain such gums could provide for bioadhesion to, e.g., buccal tissue, for buccal delivery, and the high potency of CBDA in many indications (such as epilepsy) means that a long-lasting release into tissue could require only a thin layer (thickness less than 1 mm, or preferably less than about 200 microns) of the adhesive coated-intercalate formulation. Hydrolyzing polymers such as PLA and PLGA are extremely popular in drug-delivery but are known to create acidic conditions when they undergo the (desired) biodegradation, and so are disfavored in the present invention due to the acid-labile nature of the actives herein. The matrix need not necessarily be a polymer, and simple crystalline materials such as simple salts, organic solids such as sugars/saccharides, and divalent salts of organic compounds (such as zinc N-acetyltryptophanate, see, e.g., U.S. Pat. No. 6,981, 995, the complete contents of which is incorporated by referenced herein) can also be used to bind the LDH particles together until contact with one or more body fluids-stomach acid, saliva, blood, lymph-dissolves or degrades the matrix releasing the embedded LDH particles.

Enteric coatings can be applied to particles of the invention, engendering the advantages associated with intestinal delivery. Eudragit® S 100 for example can be used to coat or encapsulate particles or films of the invention. Preferably the enteric coating comprises a coating selected from the group consisting of Eudragit™, cellulose acetate phthalate, cellulose acetate succinate, hydroxypropyl methyl cellulose phthalate, hypromellose acetate succinate, polyvinyl acetate phthalate, shellac, cellulose acetate trimellitate, zein, and mixtures or copolymers thereof.

If a coating is not applied, care must be taken in packaging embodiments of the invention, because it has been shown that contact between acidic cannabinoids and certain metals, including steel, can strongly increase decarboxylation rates. This appears to be due to a metal catalysis of the reaction. So, while intercalation in an LDH provides some protection against direct contact of CBDA with steel or other catalytic metal, there can still be danger in the presence of metal surfaces or particulates because a significant fraction of the CBDA at any given moment may be at the surface of the LDH particles; this is especially true as the particle size is reduced. The inner surfaces of any packaging material coming into contact with formulations of this invention should be free from metal. Additionally, the use of glassware for the preparation is preferred over the use of metal components.

It should be noted that formulation of THCA using LDH intercalation may require more tight exclusion of air by inert gas than in the case of CBDA, because in addition to decarboxylation, THCA also undergoes oxidation (to CBNA or CBN) much more readily than does CBDA. However, this is not likely to be a difficult engineering task because the formulation method reported herein can be performed at or near ambient temperature where oxidation rates are low.

As shown herein, CBDA stability is improved over 10-fold through intercalation in the Zinc-Aluminum LDH produced in Example 1 below. Because the decarboxylation rates of CBDA and THCA are similar (roughly within a factor of 2), it is likely that a similar Zinc-Aluminum LDH would also stabilize THCA. And using the rapid FTIR method described in Example 4, and/or the quick and easy Colorimetry tests in Example 5, one skilled in the art can find functional intercalates of the present invention for other cannabinoids by using the following process or a variation thereof:

Step 1. Use the same process and parameters used in Example 1, in particular, using $Zn^{+2}$ as the divalent and $Al^{3+}$ as the trivalent cation, at the molar ratios given in Example 1.

Step 2. Using FTIR and/or Colorimetry as described in Examples 4 and 5 resp., look for evidence of monodentate borderline chemisorption of the cannabinoid (with FTIR), and/or strongly delayed responses to the Fast Blue BB and Ferric Chloride tests.

Step 3. If Step 2 indicates success (at that level), proceed with heat-stressing followed by characterization for degradation (FTIR, NMR, HPLC, etc.), or perhaps a full-blown Arrhenius study.

Step 4. In case of failure, repeat Steps 1 through 3 using a different choice of the divalent and/or trivalent cations, until an optimal intercalate is found for the particular application.

In most applications, relative toxicities, as well as ion hardnesses, will generally be important factors in the selection of the final cations. Preferred divalent cations for the present invention are $Zn^{2+}$, $Ca^{2+}$, $Mg^{2+}$, listed in order of decreasing "hardness" of the ion; generally speaking, harder ions will yield lower aqueous solubility and, while less important at the near-ambient conditions for use of the intercalates, higher LDH stability (with heat and/or acidity), than the same LDH with a softer ion. The preferred trivalent cation for the present invention is $Al^{3+}$, and less preferably $Bi^{3+}$. The other choices are generally less favored as they are either strong oxidizers (such as $Cu^{2+}$ and $Fe^{3+}$), or readily form strongly covalent bonds with olivetolic acid derivatives and relatives, such as the bonding in bismuth subsalicylate, and a purely covalent bond with the cannabinoid is to be avoided because it creates a New Chemical Entity, as described above. Working under the limitation of $Al^{3+}$ as the preferred trivalent cation does mean that fine-tuning the hard vs. soft nature of the controlling trivalent ion can be limited; however, the other bonds and structure within the LDH naturally modulate bonding between the LDH and intercalated anion, and in fact switching from $Zn^{2+}$ to $Mg^{2+}$ was seen in this work to strongly affect the strength of the Metal-CBDA bond, and perhaps even the bond type, which for one Mg—Al LDH sample analyzed by FTIR showed evidence of being bidentate rather than monodentate, and a considerably weaker bond to CBDA as indicated by the delta value discussed below.

Additionally, mixtures of two or more divalent ions may be used to attempt to tune the bond strength. For example, if it is found that $Zn^{2+}$ as sole divalent metal ion produces too high of a bond strength (making release from the LDH difficult and slow), whereas $Mg^{2+}$ produces too low a bond strength (thus failing to protect the acidic cannabinoid from decarboxylation), then a mixture of $Zn^{2+}$ and $Mg^{2+}$ may solve both issues. The reasoning is that in the final LDH, the electronic field at any given (now singly-charged) aluminum site is influenced by multiple zinc and/or magnesium atoms surrounding the aluminum binding/adsorption site, not just a single (previously divalent) MII atom, meaning that their effects on the binding/adsorption of the cannabinoid are "blended", as opposed to creating two distinct populations of sites.

Real-time release testing (RTRT) should be performed on formulations comprising the invention, and here the extremely low solubility of the cannabinoids in water must be borne in mind, so that a simple paddle-wheel apparatus filled with water as reservoir. Rather, the receiving medium must contain either surfactant, lipid (e.g., liposomes, or emulsified lipids such as MCT oil), or organic (co-)solvent. Alternatively, mammalian tissue—particularly tissue representative of the target absorption site in the body—can be the basis of the receiving milieu, such as skin (from hairless mice, or other). Preferably, the release rate at near-expiration (that is, at or near the end of the shelf-life) is within 15%, or more preferably within 10%, of the active release rate at initial time, and in some cases this may be required by regulatory bodies.

Additional excipients and formulations. Certain embodiments of the present invention are suitable for delivery (administration) as pharmaceutical compositions, conforming to the rigorous standards of pharmaceutical production and quality control, etc.; furthermore, even embodiments intended for over-the-counter (OTC) sale and use can benefit significant significantly by adhering to at least some pharmaceutical standards of particular importance, such as adhering to excipients with a history of use in at least one pharmaceutical product with the same or similar route of administration. Such compositions generally comprise at least one LDH-intercalated Olivetolic acid derivative, i.e., one or more than one (a plurality, e.g. 2 or more such as 2, 3, 4, 5, 6, 7, 8, 9, 10 or more, or the acidic fraction of an extract) of different Olivetolic acid derivatives as actives (or modulators of activities), which may or may not demand differing LDH compositions for different actives. Accordingly, the present invention encompasses such formulations/compositions. These compositions can include one or more excipients (inactive additives) as described herein, and in some cases a pharmacologically suitable (physiologically compatible) carrier. For the purposes of the next discussion, it is best to make a rough division of excipients used as coatings, matrices, and liquid carriers, in embodiments of the instant invention.

Migration of a molecule of active (Olivetolic acid derivative) out of a layered double-hydroxide is of course necessary for in vivo release of that active molecule at the time of use by a mammal. However, premature release of the same active molecule out of the same layered double-hydroxide during the days and (more realistically) weeks before administration (that is, during the shelf-life) is to be strongly avoided, for the simple reason that the prematurely-released active may have weeks to degrade whenever that molecule is positioned outside a protective LDH. Furthermore, in the case where different LDH compositions are used to intercalate different actives, migration out of one LDH particle into another of different composition can have a detrimental effect because the active may not be as stable in the 'new' particle.

With this in mind, and returning to the useful division of excipients used into coatings, matrices, and liquid carriers, three general classes of formulations can be identified for the instant invention:

Uncoated LDH particles, optionally dispersed in a liquid or gel that is substantially free from liquids that allow solubilization of the active, such that at any location outside of an LDH particle the solubility of the active is less than about 100 micrograms/mL and preferably less than about 10 micrograms/mL; thus, certain liquid carriers (mainly aqueous solutions), and certain matrices (such as a hydrogel) are permitted, but neither should contain more than about 0.1% of, e.g., a liquid mono-, di-, or tri-glyceride, aliphatic alcohol, or water-soluble surfactant;

Uncoated LDH particles in a solid or semisolid dispersion or, adsorbed to a solid carrier; and Solid-coated LDH particles—in which the solubility of the active in the coating material is less than about 100 micrograms/mL and preferably less than about 10 micrograms/mL at the intended storage temperature during shelf-life-said solid-coated LDH particles optionally dispersed in a liquid, semisolid, or solid, or adsorbed to a solid carrier.

Thus the last classification, solid-coated intercalated LDH particles, permits the use of a very wide range of carriers and matrices, but requires a particle coating that is stripped upon administration, or alternatively, is combined just prior to administration with a second composition that strips away at least a significant portion of the solid coating, thereby allowing release of active; it is permissible that the second composition also be a solvent for the active. As an example of the latter, the solid coating could be trilaurin and the second composition triolein (a solvent for CBDA and other cannabinoids). Alcohols with chain length between 2 and 6, and more preferably between 4 and 8, such as chlorobutanol, can be particularly useful because in addition to solubilizing a coating these alcohols can delaminate layered double-hydroxides. Some examples of materials which can serve as pharmaceutically acceptable carriers (at least for some routes of administration) for solid-coated LDH particles, selected so as to be non-solvents for whatever coating is used, include, but are not limited to, alumina (as an adsorption substrate type of carrier), aluminum stearate, lecithin, serum proteins (such as human serum albumin), buffer substances (such as Tween™ 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in a composition of the third ("solid-coated intercalate") classification, according to the judgment of the formulator. In some aspects, solid-coated LDH intercalate particles are formulated in a dispensible aerosolized form in a manner that is suitable for metered dosing and the carrier is air.

In the second classification, where uncoated LDH particles are embedded in a solid or semisolid dispersion or adsorbed to a solid carrier, care must be taken to ensure against direct contact between the intercalated LDH (particularly ultrafine intercalated LDH particles) and a liquid or semisolid that is a solvent for the active. This means that the following excipients from the previous paragraph should not be substantially in contact with uncoated particles of intercalated LDH in this approach: peppermint oil; cocoa butter and suppository waxes; oils such as peanut oil, cottonseed oil, safflower oil, sesame oil, olive oil, corn oil, soybean oil, coconut oil and MCT oil; propylene glycol; esters such as ethyl oleate and ethyl laurate; sodium lauryl sulfate; partial glyceride mixtures of saturated vegetable fatty acids, waxes, polyethylene-polyoxypropylene block polymers, and wool fat. In addition, one skilled in the art will be aware that by any practical definition, solid and semisolid dispersions should be substantially free of any liquid whether a solvent for the active or not, which further reduces the list in this second classification.

In some aspects, such compositions are prepared as liquid solutions or suspensions, or as solid dosage forms such as tablets, pills, powders and the like. Solid forms suitable for solution in, or suspension in, liquids prior to administration are also contemplated. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration.

Apparatuses and methods for metered dosing (e.g., metered dose inhalers) are known in the art and are described, for example, in issued U.S. Pat. Nos. 11,109,622; 7,143,765; 5,575,280; and 5,332,378; the complete contents of each of which are herein incorporated by reference in entirety. In some MDIs a propellant is used, such as a fluorocarbon, instead of simply air.

The pharmaceutical compositions may be administered in vivo by any suitable route including but not limited to: inoculation or injection (e.g. intraperitoneal, intramuscular, subcutaneous, intra-aural, intraarticular, intramammary, and the like), topical application (e.g. of a cream, wash or lotion on or into areas such as skin, in ears or on afflictions such as wounds and burns and by absorption through epithelial or mucocutaneous linings (e.g., buccal, nasal, oral, vaginal, rectal, gastrointestinal mucosa, and the like). Other suitable means include but are not limited to: inhalation (e.g. as an aerosolized dispensable mist or spray for metered dosing), orally or buccally (e.g. as a pill, tablet, capsule, liquid, etc.), intravaginally, intranasally, rectally (e.g. via a suppository), incorporated into dressings, bandages or clothing (e.g. solid forms may be included directly in a dressing, thread or yarns impregnated with the formulations may be used to manufacture garments), etc. The formulations may be slow- or extended-release formulations. In preferred embodiments, the mode of administration is transdermal (e.g., by a film, patch, fabric/garment, spray, or cream), sublingual or buccal. In addition, the compositions may be administered in conjunction with other treatment modalities.

Application of the Invention

Once a composition containing noncovalently-stabilized olivetolic acid derivative, such as cannabidiolate-intercalated LDH particles, is obtained, this can be either administered to a human or animal, or in other applications to cell culture or bioreactor systems. In this context it should be noted that the LDH matrix is not only made of materials Generally Regarded As Safe (GRAS), but exhibits the very favorable thermal stability that is characteristic of inorganic solids and ZnAl layered double-hydroxides in particular, as shown herein.

The compositions may be prepared in dispersion form, or dried if a dry powder format is desired. The choice depends on many factors specific to the particular setting, such as the increased risk of migration (as discussed herein) and incremental cost in transporting a (relatively concentrated) liquid dispersion over that of a dry powder, versus the incremental cost of drying the dispersion. In situations where a dry powder is preferred, it may be advantageous to add one or more disintegrants to the dispersion prior to drying. Useful disintegrants include, but are not limited to, croscarmellose, pregelatinized starch, sodium starch glycolate, soy polysaccharides, papain, and mannitol.

The pH conditions encountered by the produced particles are not extremely critical, as LDHs are generally stable except at very acidic pH; indeed, Iyi et al. [Chem. Mater. (2004) 16:2926] showed that even in 0.0025N hydrochloric acid, LDHs are relatively stable unless the salinity is very high, in which case anion-exchange takes place. Generally, in most applications of the invention, acidic conditions should be minimized or avoided in the final, complete formulation, since certain acids may be able to migrate into contact with the acidic cannabinoid and cause decarboxylation; this is especially true for acids that are not of high MW, viz., acids with MW less than about 2,000 should generally be avoided or present only in de-protonated, salt form.

High concentrations of active olivetolate derivatives are possible in this invention when reduced to a powder comprising one or more LDH-cannabinoid intercalated layered double-hydroxides. In particular, cannabinoid concentrations between 0.1 and 20 wt % are readily attainable in the practice of the invention, and even a low loading of 0.1%, or 1 mg/gm, would provide 1 mg of CBDA in a sugar cube sized dosage form of LDH-CBDA, and evidence at the time of this writing is that a 1 mg dose of CBDA can be efficacious for many applications such as nausea and epilepsy (see, e.g., U.S. Patent App. #20180228751 to Stott). Additionally, the above-cited loading of 3.5 meq/gram, if achieved, would yield a loading of just over 50 wt %.

The layered double hydroxide $MgAl$-$LDH$-$CO_3$ is widely administered in humans as an antacid, and numerous studies have shown this LDH to be safe for consumption and quickly cleared from the body. Even LDH nanoparticles within the size range of 100-200 nm have been shown, in human lung cell cultures, to exhibit very low cytotoxicity in terms of cell proliferation, membrane damage, and inflammation response. For application of the LDHs of the present invention in the Supplements market (viz., not necessarily in more sophisticated Pharmaceutical applications), milling to nanometer size is overkill, and particle sizes greater than 5 microns may be most preferable in oral administration.

If an intercalated LDH formulation of this invention, even one with other elements such as an outer coating, is dosed to an individual (or mammal) every day—as would generally be the case in a therapeutic application—then the dosing should be very similar as with hemp oils and other CBDA products, except perhaps for a longer time to the initial onset, for the following reason. If two formulations of the same drug are given at the same daily dose, and the formulations do not simply pass through to excretion without releasing drug, then the only effects of a slower release are: a) longer time for the initial onset of effects, which could extend to several days if the release takes days; and b) a more constant blood concentration, once steady state has been reached. The reason is simple: after roughly a week or two of dosing, the same amount of drug has been released, and excretion is only minorly affected by drug formulation, if at all. Certainly, this rule of thumb has exceptions in special cases, but the inventor does not foresee these playing an important role in the application of this invention, at least in daily peroral dosing. This greatly simplifies the issue of finding a dose for a new formulation of a known drug or active.

Screening a formulation for the desired pharmacologic (therapeutic) effect may be possible even prior to human or animal model testing, in the event that an in vitro test is available with good in vivo/in vitro correlation (IVIVC). For example, when the indication is epilepsy, one known screen utilizing an amoeba is described below.

An outline of a clinical trial designed to establish the effect of LDH-intercalated CBDA for anxiety, post-traumatic stress disorder (PTSD), and potentially other mood disorders, using buccal delivery, can now be given. By way of background, in NCT02902081, cannabidiol (CBD) in highly purified form Epidiolex®, purified exhaustively to be less than 0.1% CBDA—was given orally to 38 human subjects at doses as high as 900 milligrams, and no significant therapeutic effect was seen in affect in the International Affective Picture System, with measurements of arousal remaining unaffected at 300, 600, and 900 mg doses. The same evaluation methodology (the IAPS), including the overall test design and criteria, would be used for a test of the present invention except that the drug product would be a buccal spray based on a CBDA-intercalated zinc-aluminum LDH prepared with the molar ratios and other parameters (viz., molar ratios) used in Example 1, or possibly a more optimized variation thereof. A slow-release, buccal-targeted spray formulation of this intercalate could offer many advantages over the oral CBD used in NCT02902081:

Potentially much higher drug potency than CBD;
Improved bioavailability over a simple oral formulation, particularly to the CNS;
More constant release rate and blood levels, due to direct contact with lipidic cell membranes and compartments that solubilize cannabinoids;
Potential avoidance of Blood-Brain Barrier disruption;
Taste-masking (an advantage obviously partially offset by the buccal delivery selection);
Ease and flexibility of use and dosing, with relatively rapid onset for "use-as-needed" pharmacokinetics;
Ease and flexibility of manufacture, requiring only 3 reactants (besides CBDA itself), an aqueous reaction medium, non-toxic solvents (e.g., fats), and ambient reaction temperatures;
Low costs of excipients/reactants; viz., the prices of metal nitrates are miniscule compared to the (unavoidable) cost of the active, and solvents are inexpensive as well;
Potential further reduction in production/sourcing costs and issues if intercalation is used to selectively extract the acidic cannabinoid CBDA and reject CBD (important since the CBD:CBDA ratio is highly variable in extracts of natural source);
Availability of rapid QC methods such as FTIR and Colorimetry as delineated in detail herein;
Relatively high drug loading, with final CBDA concentration in the particles of the formulation-discounting the rapidly-absorbed liquid carrier, but counting any coatings—of at least 40 mg/mL with 200 to 400 mg/mL being readily achievable.

Once the CBDA-LDH intercalate is produced (under no requirement of Sterile Manufacture), the washed and dried particles would be milled to a volume-weighted size average targeted at 10 microns, corresponding to maximal deposition, from a Metered Dose Inhaler (MDI), into the buccal and upper pharynx regions and minimal or at least acceptable deposition down into the bronchi. Preferably the D90 of the volume-weighted size distribution is less than 50 microns, and the D10 greater than about 5 microns since bronchial uptake increases greatly below a particle size of about 4.7 microns. If possible, the kinetics of the co-precipitation would be tuned so that the primary crystallite size was very close to 10 microns, and methods of homogeneous nucleation for example, are known that produce narrow distributions in crystal size. A 10-micron powder would first be tested, preferably beginning with a mammal model, using standard MDI materials and methodologies, for one or more physiological or pharmacological endpoints such as CBDA blood levels, etc. If uptake is considered successful, and ultimately an estimate of the bioavailability is determined, then the dose of powder would be calculated from the known CBDA loading and the desired CBDA blood levels and/or AUC (Area Under the Curve of the blood level profile vs time). Based on current knowledge, more on the order of 1 mg—rather than 900 mg—would be the desired delivered dose. As discussed herein, coatings of bioadhesive polymers, such as sodium alginate, in the salt form and thus substantially de-protonated, and of sufficiently high MW (preferably greater than 2,000 MW), can be used to coat intercalates of the invention so as to provide bioadhesion, that is, to promote adhesion to tissue such as buccal or the pharynx. (It is known that while Carbopol polymers are also commonly used bioadhesive coatings, they are not well suited for buccal delivery because of their tendency to expand over tissue thus breaking adhesion—at least when applied as a film, and even a particulate spray can produce an adsorbed film at high enough surface coverage). One with skill in the art will recognize that a number of scalable, long-established methods of particle coating can be applied in an economic fashion to produce polymer-coated LDH intercalate particles of controlled 10 micron size, including spray-drying, chemical precipitation, coacervation, emulsion polymerization, etc. Since sodium alginate is basic and chosen to be of MW greater than 2,000 it presents a minimal decarboxylation threat to the CBDA during the shelf-life of the product, as per discussions herein, and absent any organic liquids in the formulation, should also present minimal risk of CBDA de-intercalation and migration out of the LDH. In summary, within the scope of this invention is a readily and economically manufacturable Metered Dose Inhaler formulation of CBDA with the thermal and oxidative stability demonstrated herein for at least 6-month shelf-life with <10% loss of potency, which is a free-flowing powder with high CBDA loading, and of a particle size and surface characteristics suited for delivery and at least modest adhesion to the targeted tissue, namely the buccal (and nasal) tissue and upper respiratory tract. Other acidic cannabinoids may be so formulatable as well. Potential applications, with at least some support in the literature, for CBDA and potentially this (or a similar) embodiment of the invention include a range of mood and anxiety disorders both chronic and acute, exemplified by post-traumatic stress disorder (PTSD), anorexia, depression, drug addiction, social phobia, schizophrenia, bipolar disease, psychosis, and generally in indications where 5-HT1A receptors are involved.

Additionally, an outline for development of a product based on the current invention for treating nausea and anticipatory nausea (conditioned gaping) in, e.g., cancer patients, is now provided. By way of background, an established animal model (see, e.g., Bolognini D. et al., Br *J Pharmacol.* 2013; 168(6)) has shown that CBDA—at doses as low as 0.01 mg/Kg—suppresses lithium chloride- and cisplatin-induced vomiting in mice and shrews as well as motion sickness, proving much more potent than CBD, and that same cited publication also contains detailed in vitro receptor binding/displacement studies that provide the basis for a simple screen of candidate formulations in optimization work. While the approach described above for producing medicated (CBDA) garments could be used to produce a CBDA hat/cap or compression sleeve for this indication, a product with as fast release kinetics as possible, without requiring injection, should for CBDA be a sublingual formulation analogous to fentanyl or nitroglycerine (both fairly hydrophobic with partition coefficients of Kow=860 and 42, resp.). An enabling description for manufacturing tablets for sublingual use is provided in U.S. Pat. No. 6,500,456B1 to Capella, and a manufacturing process built on that would be applied to a powder of the current invention, manufactured and tested as described herein. While Capella had to deal with the loss of content uniformity due to migration of nitroglycerine in some tablet compositions, that problem is expected to be less in the case of a CBDA intercalate, provided that oily and strongly ionic components (such as magnesium stearate) are avoided. Preferred (solid) excipients for such tablets, if needed for disintegration as determined by formulation screening, would thus be selected from the group consisting of lactose, (fumed) silica, pregelatinized starch, and glyceryl monostearate; silica is thus much preferred over alkali metal salts; polyethylene glycol is best avoided unless the molecule is of MW greater than 3,000 and preferably end-capped, as glycols can induce decarboxylation.

And, an outline can now be given for the development of an embodiment of the present invention for oral delivery of tetrahydrocannabinolic acid (THCA) in the treatment or prevention of Huntington's disease, and possibly other neurodegenerative and neuroinflammatory diseases, where the neuroprotective PPARg agonist activity of THCA is known to be much more potent than that of THC. To begin the development, a layered double-hydroxide composition, perhaps different from that in Example 1, would be found by screening a range of compositions for thermal stability of the THCA-LDH intercalate, using the procedures and rapid screening methods described herein which include heat-stressing at a higher temperature such as 80° C., Colorimetry and spectroscopy (such as FTIR, NMR, etc.). Once a stabilized formulation is found, a milled THCA-LDH intercalate is coated using established means of fine particle coating, such as spray-drying, to coat the particles with an enteric coating such as Eudragit S100. Using well established compression methods tablets are then made from the coated particles, with proper attention paid to the use of lubricants and disintegrants as known to one skilled in the art. The tablets would then proceed on to stability, release, animal tests, and finally clinical testing.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1

A cannabidiolate-intercalated layered double hydroxide of the Zn—Al type, herein abbreviated LDH-CBDA$^{1-}$, of the present invention was produced by co-precipitation using zinc and aluminum nitrates. The cannabidiolate ions were provided directly from "Alleviate X" CBDA formulation in MCT (from 101 CBD, Ventura, CA). Zinc nitrate hexahydrate, in the amount 0.37 grams, and 0.156 gm aluminum nitrate nonahydrate were dissolved in 4 mL decarbonated water under inert gas. A 2M solution of sodium hydroxide was also prepared under nitrogen flow using decarbonated water. Approximately one-fourth of the nitrates solution was first adjusted to near neutral with NaOH, to avoid exposure of the CBDA to strongly acidic conditions; only a small amount of precipitation resulted, and contact with the solution of CBDA in MCT with strong magnetic stirring was made within a few seconds of this neutralization of the nitrates solution. With strong stirring and under nitrogen atmosphere, and with the mixture of CBDA/MCT oil phase kept continually in contact with the aqueous phase by the stirring, the (acidic) nitrates solution was added in aliquots alternately with the (basic) NaOH solution, to precipitate LDH by rise of the pH, with the final pH being approximately 10.5. A fine particle size of the precipitated LDH was indicated by the very slow settling of solids observed prior to centrifugation. Due to the cannabinoids, the mixture was greenish-yellow colored, although without centrifugation, it could not be determined how the colored cannabinoids were distributed between the various phases present.

Twenty hours after the start of the reaction, the entire reaction mixture was centrifuged at 3,000 rpm in a refrigerated floor centrifuge for 30 minutes. Three regions were clearly separated. The top region was a thick, greenish-yellow colored dispersion of layered double hydroxides dispersed in MCT oil; the yellow-green coloration, combined with the fact that the density of these LDH solids appear to be less than about 1 gm/mL since they centrifuge above the aqueous solution, strongly indicates that these LDH solids are substantially intercalated with organic material, namely cannabidiolate anions. The center region was nearly colorless water. The bottom layer was also rich in LDH particles. A digital photograph of the test tube was taken and the two LDH layers analyzed for color at the PHP Tools website; the dominant color codes reported were #d8d890 for the low-density LDH layer and, for the high-density bottom phase, a 50:50 mix of the off-white colors #f0f0d8 and #d8d8c0:

Top, low-density region:

| Color Code | Percentage |
|---|---|
| #d8d890 | 85.3% |
| #c0c060 | 12.7% |
| #c0a830 | 1.6% |

Bottom, high-density region:

| Color Code | Percentage |
|---|---|
| #f0f0d8 | 51.0% |
| #d8d8c0 | 49.0% |

In terms of CMYK values, that for the top layer was {0%, 0%, 33%, 15%} (note the high Yellow component), whereas that for the bottom layer (using #f0f0d8) was {0%, 0%, 10%, 6%} obviously nearly white.

After the first centrifugation, the middle, aqueous phase was removed by syringe, and nitrogen-sparged cyclohexane added (3.9 gm), with vigorous shaking. Cyclohexane was chosen as a wash due to the implied relatively low solubility of cannabidiolate in that MCT-miscible solvent; the Hildebrand solubility parameters for CBDA and cyclohexane, which are 25.8 and 16.8 resp., differ by 9. This made it possible to remove the MCT with this washing step. Following this wash and the removal of the lightly colored MCT phase, another wash with decarbonated water was followed by centrifugation and decanting of the water phase. The resulting LDH-rich dispersion was then dried under nitrogen. The final powder was then examined first for color, and the CMYK values were 0|3|10|4 (color code #f4eddc) which is nearly completely white, and with little to no evidence of the pinkish coloration associated with oxidation or oxidative decarboxylation. In a different batch made in the presence of atmospheric oxygen, a strong pink color resulted, with CMYK values of 0|12|18|5 (color code #f1d3c5), thus with 4-fold higher Magenta contribution.

Figure 7A:
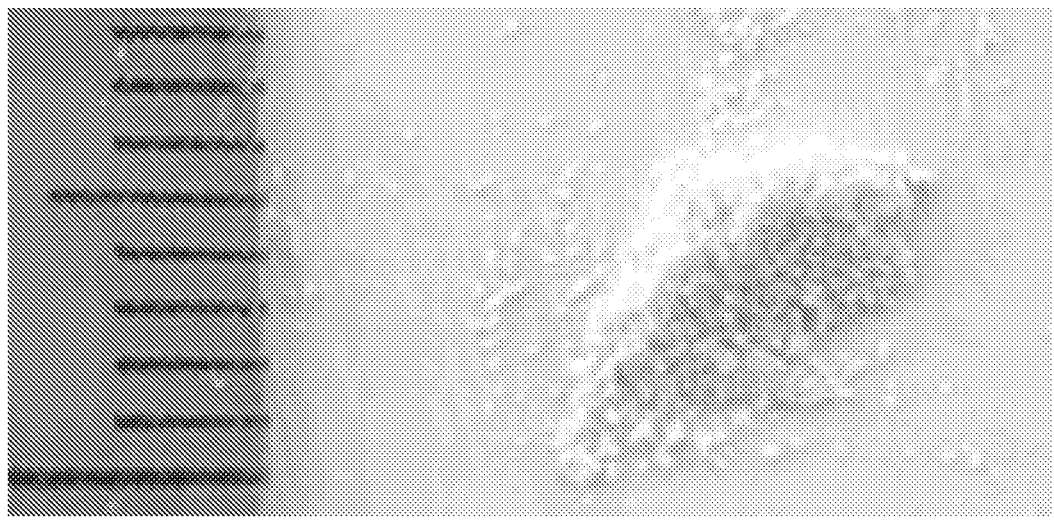
FIG. 7A-C. A, Photograph of a free-flowing powder made of LDH-CBDA intercalate of the invention, where no milling or other particle-size reduction has been carried out. Each marking on the ruler at left is 1 millimeter; B, Photograph of the same powder as in A, but spread out so as to reveal the angularity of the particles. Each marking on the ruler at left is 1 millimeter; C, Optical micrograph of the free-flowing powder of the invention, where no milling or other particle-size reduction has been carried out, demonstrating the very fine size and the angularity of the intercalate. In particular, the primary crystallite size is less than 5 microns in this sample.
Figure 7B:
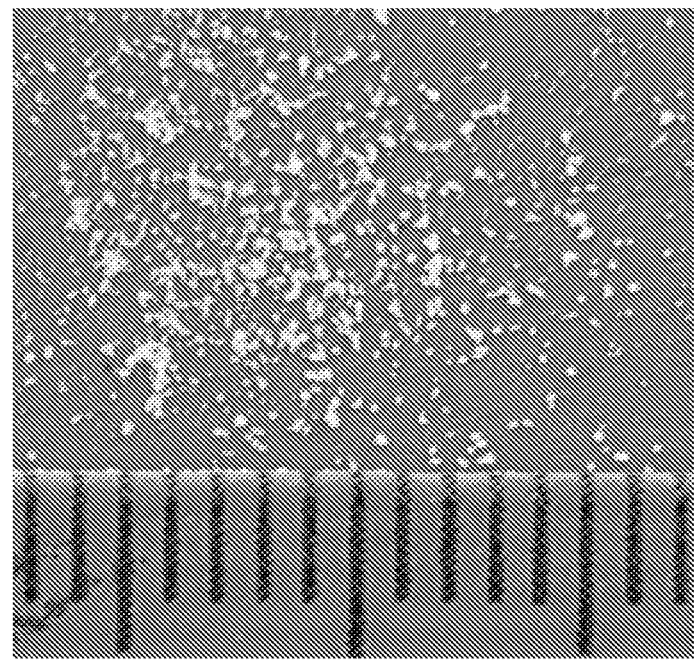
Figure 7C:
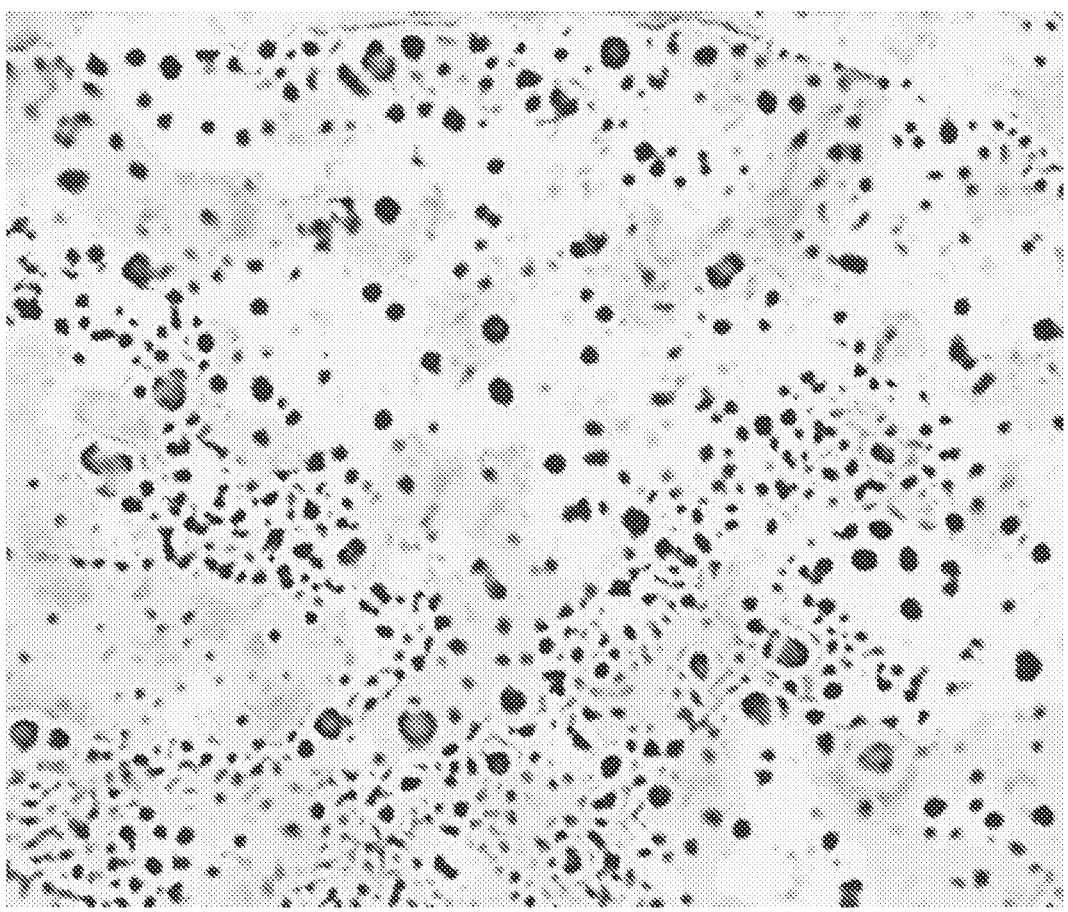

Optical microscopy was performed on the washed and dried dispersion, using a Nikon Optiphot microscope in transmitted light mode with a 20× objective. FIGS. 7A-C show exemplary micrographs. This clearly showed crystals, angular and roughly hexagonal-like in cross-section. Primary crystallite size was between 1 and 5 microns. Mild sonication reduced the degree of aggregation of these primary crystallites, yielding a finer appearance to the solid. This is all consistent with the known behavior of Zn—Al layered double hydroxide materials.

The combined weight of the evidence clearly shows that an embodiment of the present invention, namely a Zn—Al layered double hydroxide material intercalated with cannabidiolate ions, was produced in this example. Next, the thermal stability of this formulation was semiquantitatively analyzed using Thin Layer Chromatography (TLC), and then analyzed with ATR-FTIR, and the stability shown to be far better than any CBDA-containing formulation for which thermal stability data have been reported, to the inventor's knowledge-recognizing that the agreement of stability data (e.g., half-life of CBDA) amongst those studies known from the literature provides a benchmark that is very difficult to improve on substantially, without use of the present invention, for reasons given herein.

Example 2

The above LDH-CBDA$^-$ formulation was analyzed using TLC, and the results compared with stability data from the Citti et al. and Wang et al. groups. The parameter best represented by the analysis is given by a measure that will be denoted P, the CBDA potency retention as a function of heat-stress time, using molar concentrations:

$$P=[\text{acidic CBDA}]/([\text{acidic CBDA}+\text{decarboxylated CBD}]).$$

While the presence of THCA and THC, and possibly other cannabinoids, can potentially affect the measure P, this is of less importance herein, because:
  a) The initial amounts of THC and THCA are very low in the "Alleviate X" tincture, and these compounds cannot be created in any substantial amounts in the MCT tincture;

b) Even if THCA were more abundant, it is known that the decarboxylation rate of THCA to THC is not vastly different from that of CBDA to CBD (the values of the first-order rate constant k for CBDA and THCA decarboxylation at 100° C. were reported as $4.13 \times 10^{-4}$ and $4.93 \times 10^{-4}$, resp.; for the latter, see [Perrotin et al., Journal of Molecular Structure 987 (2011) 67-73].

Thus, P in this case is expected to be close to CANA/CANtot, using more conventional notation.

Cannabinoid-containing samples including one from a CBDA-rich hemp extract (source: 101 CBD, Ventura, CA) were compared on a thin-layer chromatography (TLC) plate, and the results compared with the vendor analyses, which it can be surmised was taken within a few weeks of extraction from hemp. The TLC cannabinoid method used was adapted from Meatherall and Garriott [Journal of Analytical Toxicology, Vol. 12, May/June 1988]. Sampled amount was dissolve in a 3:1 chloroform:methanol mixture, then transferred via a glass capillary tube to a silica-based TLC plate. By volume, the mobile phase was a 90:9:1 liquid mixture of hexane, 1-pentanol, and glacial acetic acid. Approximately one hour was needed for the solvent front to advance sufficiently. TLC plates were then removed and dried with a heat gun, then stained by immersion in an aqueous triethylamine solution, rinsed, and stained with a permanganate-based stain, or in some cases with a Fast Blue BB stain solution that confirmed the reddish and orange cannabinoid signatures well known with Fast Blue BB.

For the untreated "Alleviate X" tincture, CBDA:CBD ratios of approximately 4:1 were confirmed in the present disclosure by direct experiment under TLC plate analysis, with objective identification and quantification of TLC spots using the online service "JustQuantify", resulting in particular in an experimentally measured ratio of 4.73:1 (or P=0.825). This is clearly consistent with the ratio quoted by the supplier, as the supplier provides analyses on their website which, at the time of this writing, indicate a CBDA:CBD ratio of 4.10 (or P=0.804). Essentially all the non-acidic cannabinoids, mostly CBD with some THC and CBN, migrated all the way to the solvent front, that is, exhibited a relative retention of near 1.0, whereas the acidic cannabinoids lagged behind with an $R_f$ value of approximately 0.85, as was reported by Meatherall and Garriott.

Then, a sample of 60 mg of the LDH-CBDA$^-$ material from Example 1 was held in an 80° C. oven for 64 hours, with inert gas in the test tube head space. After cooling, the following co-solvents were added to this 60 mg sample delaminate the LDH and release the cannabinoids: 63 mg pentanol, 76 mg glacial acetic acid, 103 mg of dimethylformamide (DMF), and finally 187 mg of a 3:1 chloroform:methanol mix to prep for TLC. Crucially, the final solution was perfectly clear, with no detectable suspended solids or extraneous phases.

The raw tincture as received from 101CBD was first stressed at 80° C. for 2 hours and 4.5 hours, then these stressed and an unstressed sample were analyzed by the TLC method described above. The output from the "JustQuantify" online analysis of photographs of the TLC plates is shown in FIG. 1 as Ln(P) vs hours heated, and a regression line computed using Microsoft Office Excel. From the graph the decay constant is determined at this 80° C. temperature to be approximately k=0.22/hour, or $6.2 \times 10^{-5}$ sec$^{-1}$, which is in excellent agreement with the value $5.35 \times 10^{-5}$ sec$^{-1}$ reported by Wang et al. The half-life is estimated to be 3.1 hours (Wang's estimate being 3.6 hours).

Amazingly, a sample of the intercalated LDH prepared as described in Example 1, subjected to 64 hours of this same 80° C. temperature, gave a TLC result of P=0.596 meaning only 40.4% loss of potency—that is, the half-life of this formulation as per the invention is over 64 hours, and is best estimated as 86 hours, from a calculated decay constant of $k=2.2 \times 10^{-6}$ sec$^{-1}$ or 0.008 hr$^{-1}$. Thus, this formulation as per the present invention increased the half-life of CBDA by a factor of approximately 17.

An approximate seventeen-fold increase in half-life of CBDA, uniquely made possible by the present invention, can be roughly extrapolated to temperatures closer to ambient. Wang's data extrapolate to approximately 3.7 weeks at 25° C. before hitting the critical 10% degradation point; note that this figure was approximately the same for Wang, Citti, Ceriliant Analytical Reference Standards Inc., and the present work, and so this figure seems to be resilient from a range of prior art formulations that include pure CBDA, acetonitrile solution, hemp oil, and a CBDA-rich hemp extract. Ratioing directly to those data, the present data would yield, using the same extrapolation parameters, an estimated time to 10% degradation of 63 weeks, thus over a year. Therefore, already this invention is projected to yield a full year of shelf-life even under the strict FDA guidance of <10% degradation in 12 months, a stability hurdle that is the norm for intravenous drug formulations for example, exemplifying the high degree of product confidence that this 10% limit assures.

It should also be pointed out that because LDHs are opaque, the encapsulation in an LDH as per this invention also provides strong protection against light-promoted degradation. This means it can decrease degradation rate whether or not the main stressor is light (esp. UV), or the light works together with thermal stresses. Fine primary crystallites scatter light, and the LDH composition itself has significant absorption of UV light to provide additional photoprotection [see, e.g., FIG. 9 in Mohsin et al., *Int J Nanomedicine*. 2018; 13: 6359-6374]. Additionally, UV absorbers with an acidic group, such as Eusolex® 232, can be intercalated together with the cannabinoid, in the present invention.

Additionally, the cannabinoid-intercalated LDH produced herein was found to lack the objectionable odor and off-taste of the raw cannabinoid isolate. Thus, potential medicinal products enabled by the present invention include a broad range of oral products formulated in sublingual forms, buccal films and sprays, and liquids. Additionally, potential consumer beverages containing dispersed LDH-cannabinoid, such beverages potentially including wine, uncarbonated drinks, coffee, tea, and sports drinks. Carbonated beverages may interfere with some of the effectiveness of intercalated LDH's because carbon dioxide and carbonate ions have a very strong affinity for the LDH, and while their ability to displace cannabinoid anions may be limited by the low solubility of the cannabinoids in water, the presence of other taste components (such as the essential oils in many soda drinks such as Coca-Cola® or the alcohol in stronger drinks, could increase this solubility, resulting in "free" cannabinoid (non-intercalated). Another application of the invention would be in providing cannabinoid functionality to frozen treats such as ice cream without incurring the off-tastes and TRPV1-induced "heat" of the common cannabinoids.

Example 3

This Example demonstrates the ability of the methods and materials of this invention to selectively extract acidic cannabinoids over non-acidic compounds, from complex cannabinoid mixtures developed from Cannabaceae plants and other sources of cannabinoids including but not limited to cell culture, yeast fermentations, and chemical syntheses.

A hemp-derived isolate rich in cannabigerolic acid (CBGA>95%), in the amount 1.0 gm, was dissolved in 3 mL chloroform to form the hydrophobic phase of a two-phase system. The aqueous phase consisted of 5 grams zinc acetate dihydrate and 2.1 grams aluminum nitrate nonahydrate dissolved in 60 mL of decarbonated water. Sodium hydroxide solution (1M) was then added to bring the pH to 6.5 before adding in the chloroform phase. The two phases were combined with a magnetic stir bar strongly agitating the mixture. The NaOH solution was then added gradually, causing precipitation of an LDH, to a final pH of 10. After 8 hours of reaction time, the mixture was centrifuged at 3,000 RPM for 20 minutes, after which the precipitate was dried under warm air flow. No washing away of the excess water-soluble reactants was considered necessary, as they were anticipated to have little effect on the cannabinoid analysis. The material was held below freezing up to the point of analysis.

For analysis, isopropyl alcohol and hydrochloric acid were applied sequentially to delaminate the (intercalated) LDH and release the cannabinoids through dissolution of the inorganic matrix (i.e., the LDH). HPLC was then performed using the well-known "Dutch" method using formic acid.

The table below shows the results of the HPLC analysis of the starting CBGA-rich "isolate", compared with the LDH-intercalate produced; concentrations are given in weight percent. As clear from the table, the only cannabinoids detected in the LDH-intercalate of the invention are CBGA, and a small amount of CBG. Thus, while the invention extracted a strong loading (over 9 wt %) of CBGA, the non-acidic CBD and CBC were not detectable in the intercalate despite being present in the starting isolate. Concerning the presence of CBG in the intercalate, two facts should be noted. First, CBG is the decarboxylation product of CBGA, and therefore could have been produced by slight degradation of the intercalated CBGA, thus not requiring any direct intercalation of CBG at production. And second, even if all the CBG (0.20%) in the isolate had been intercalated, it would not have accounted for the 0.26% CBG in the intercalate measurement, meaning that at least some of the CBG must have come from some degradation of CBGA. It is believed that some, if not most, of the degradation actually occurred during the step that used a solvent mix to release and dissolve the active for subsequent HPLC, as the procedure involved formic acid, and did not adhere to the anhydrous pentanol-based method described herein. Also, it should be noted that while intercalation of CBGA was confirmed in this experiment, this does not necessarily mean that the CBGA is substantially protected from decarboxylation or oxidation, because the molecular configuration and strength of the bond to the LDH may not be as needed, having switched from CBDA to the more flexible molecule CBGA, with 7 and 10 rotatable bonds, resp., resulting in more steric interference with the cannabinoid-LDH bond, and with differing pKa's (3.4 and 2.9, resp.), etc. In particular, a monodentate bond with a bond energy near 48 kJ/mol, identified for example by a value of the FTIR-measured delta ($\Delta = \upsilon_{as} - \upsilon_s$) near 139 cm-1 as described below, is shown herein to correlate with, and potentially guarantee, high stability against decarboxylation and oxidation.

| Cannabinoid | Isolate | LDH-intercalate |
|---|---|---|
| CBN | <0.01 | <0.01 |
| $\Delta^9$ THC | <0.01 | <0.01 |
| CBDV | <0.01 | <0.01 |
| CBG | 0.20 | 0.26 |
| CBD | 0.30 | <0.01 |
| CBC | 0.06 | <0.01 |
| CBDA | 0.22 | <0.01 |
| CBGA | 98.95 | 9.14 |
| THCA | <0.01 | <0.01 |
| THCV | <0.01 | <0.01 |

Thus, the methods and materials of the present invention could potentially be used to extract acidic cannabinoids selectively from complex mixtures/extracts, and potentially formulated these acidic cannabinoids at the same time-purification and formulation both in a single step. Particularly with the use of the two-phase reaction demonstrated herein, the organic phase containing the acidic cannabinoid targets can also include non-acidic compounds that will be only minimally intercalated and would be substantially left behind in the organic phase once the LDH-intercalate is harvested by some combination of centrifugation and/or filtration. Indeed, it may be possible to use a crude hemp oil extract as the entire organic phase, perhaps only mildly diluted or even undiluted. Methods are known and utilized in this field for using terpenes, even from the plant itself, to solubilize cannabinoids, providing yet another method of making the present invention involving an aqueous phase containing the LDH precursors and a second phase containing the cannabinoids in a phytochemical milieu. Such methods of extraction/formulation of CBDA, CBGA, THCA, CBCA, CBDVA, THCVA or other natural or synthetic acidic or anionic cannabinoid, or mixtures thereof, or in the extraction and formulation of amorfrutins from plant extracts, may be more efficient and economical than extraction methods based on distillation, preparative HPLC, or other methods (which often require heat, thus promoting decarboxylation, or toxic organic solvents), and furthermore can produce a stabilized, powder formulation of the final acidic cannabinoid(s) extracted. Conceivably such a process could even be performed in continuous-mode operation, with a stream of hemp oil (or terpene-solubilized cannabinoids) encountering LDH-forming conditions (e.g., divalent and trivalent nitrates in aqueous solution contacting the oil stream and added base).

The present invention can be used to extract and/or formulate acidic cannabinoids not only from plant extracts of the Cannabaceae family, but also from cannabinoid-rich excretions created using yeast, bacteria, fungi (e.g., *Pichia pastoris*), potentially genetically-modified organisms. For example, Bacterium *Zymomonas cannabinoidis*, a gene-edited version of *Zymomonas mobilis*, has been engineered to produce a full sprectrum of cannabinoids. See for example U.S. patent application 20160010126A1, and WO2017139496A1 for methods that produce cannabinoid mixtures.

It is widely recognized in the pharmaceutical arena that fine, free-flowing powders are an excellent starting point for many types of formulations, and are required for certain methods and equipment used in formulating pills, suspensions, dispersions, and other particulate forms. Fortunately, the intercalated LDH produced in the experiments reported herein is, indeed, a free-flowing powder, in sharp contrast with the sticky, greasy isolates that are current forms of CBDA, THCA and (to a lesser extent) CBGA. Without wishing to be bound by theory, it appears the tar-like compounds that give these cannabinoids the reputation of being extremely sticky are not highly expressed on the surface of the solid particles making up the powder. This is supported by the pure-white appearance of the intercalate. That is, a tarry compound intercalated in an LDH appears to have its stickiness and discoloration "hidden" by the LDH, whereas one would expect stickiness (and perhaps) discoloration even using an LDH if the same compound ended up at the outer surfaces of the particles or solid; the absence of stickiness in the powder thus seems to indicate that the acidic cannabinoids are confined to the interior of the solid particles, and migrate only very slowly, if at all, to the surface, as demonstrated herein by the Colorimetry tests in Example 5 below. In the event a particular method and composition of the present invention results in a problematic amount of stickiness in the powder, it should be possible to reduce this by washing the powder with a decarbonated solvent, working quickly to minimize extraction of intercalated active.

Contrarily, rather than using fine powder formats of the invention, larger intercalated LDHs can be produced from scratch—i.e., without need for tablet compression methods—which could be useful as solid, macroscopic chunks of solid that might be appropriate for certain OTC (over-the-counter) applications, including but not limited to a "candy-like" product that can be licked; indeed, lollipops with medications have even been effective as hospital products (primarily for pediatric use).

Example 4

Attenuated-total-reflectance FTIR (ATR-FTIR) was used to analyze both heat-stressed and unstressed embodiments of the present invention, with the CBDA-rich cannabis extract intercalated in a Zinc-Aluminum layered double-hydroxide as described in the previous Examples. Spectra were then compared with the those of same extract, both stressed and unstressed samples. Interpretation of peak positions was informed by simple analyses in the open literature on CBDA and CBD, as well as related compounds.

FTIR spectra were collected on a Thermofisher Nicolet iS50 spectrometer using the attenuated total reflection (ATR-FTIR) method. The ATR crystal was diamond, and the detector was a deuterated triglycine sulfate (DTGS) detector. The data collections used 32 scans with resolution 2 in which the data spacing was 0.241 cm$^{-1}$. In the advanced ATR correction data processing, the refractive index of the samples was set to be 1.5, which is appropriate in view of the known refractive indices of zinc hydroxide (1.38), various LDHs (1.54-1.55), and CBD (1.55), all of which are well under that of diamond.

The decarboxylation of CBDA to CBD, or other degradation product lacking the carboxyl group, must of course lead to some changes in the FTIR peak positions and intensities for carboxyl-associated groups on the CBDA molecule; these peaks are readily found from, e.g., literature data, where a certain peak position in the CBDA spectrum changes and in particular when it is essentially absent in the CBD spectrum, and additionally supported by the large volume of knowledge on FTIR analysis of carboxylic acids. Both the present study and published literature agree that there exist 8 carboxyl-associated peaks that shift upon decarboxylation, and these are listed in Table 1 below: Table 1.

TABLE 1

Shifts expected in carboxyl-associated peaks for CBDA at:

| Peak position (intensity) | Proposed assignment |
|---|---|
| 763 (mw, broad) | $\delta(C=O)$ carboxyl |
| 887 (m) | $\delta(OH \ldots O)$ carboxyl |
| 1110 (mw) | $\nu(C-O\,[=O])$ carboxyl |
| 1183 (m) | $\nu(C-OH)$ phenolic 2-OH/4-OH |
| 1257 (s) | $\nu(C-OH)$ carboxyl |
| 1301 (m) | $\delta(O-H)$ phenolic 2-OH (ortho) |
| 1501 (m) | $\nu_s$ carboxyl |
| 1621 (vs) | $\nu_{as}$ carboxyl |

The position (in cm$^{-1}$), relative intensity (in parentheses, from vw=very weak to vs=very strong) and proposed vibrational assignment (usual FTIR notation) for the main carboxyl-associated peaks seen in the spectrum for neat CBDA; these peaks can be expected to shift position upon intercalation into an LDH due to the strong electrostatic interactions between acidic cannabinoid and the layered double-hydroxide.

It must be emphasized that these eight carboxyl-associated peaks can change in TWO distinct ways, due to TWO possible mechanisms, in the preparation of an embodiment of the invention:

Intercalation (dramatic change in ionicity of milieu); SHIFT in peak position observed;

OR

Decarboxylation (loss of carboxyl group); LOSS of peak intensity observed.

Figure 2:
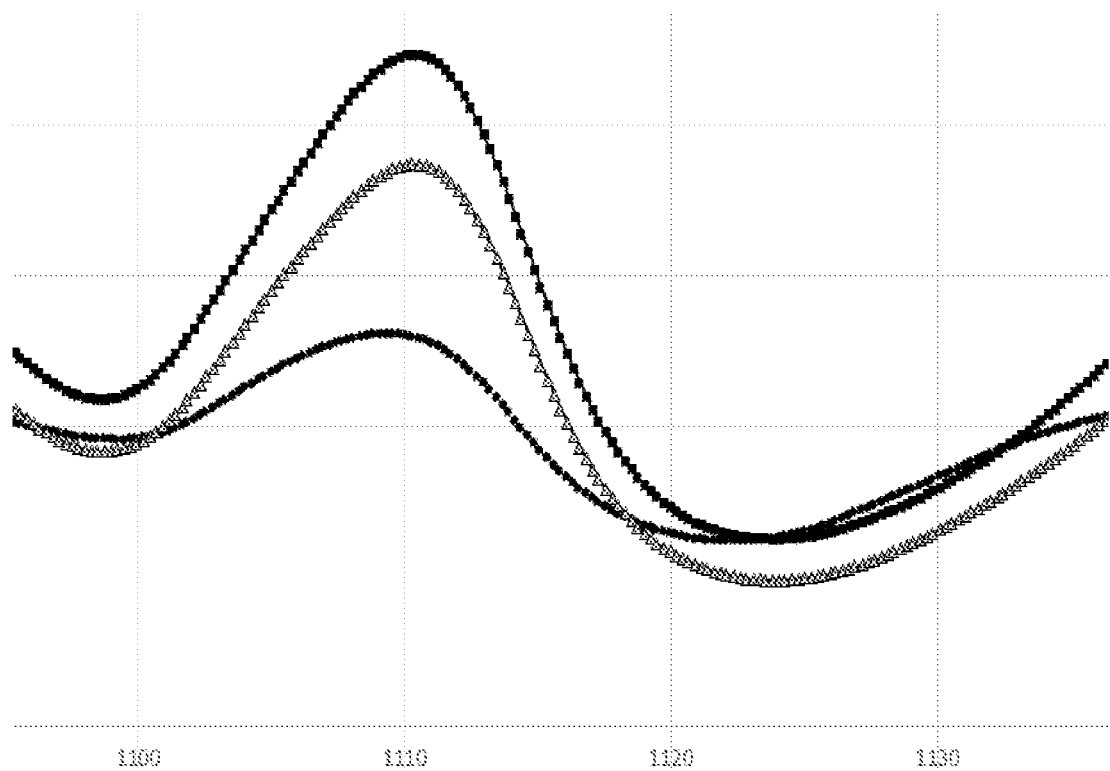
FIG. 2. FTIR spectra of CBDA-rich extract Control, abbreviated herein as "neat CBDA", revealing progressive loss of the peak at 1109 $cm^{-1}$ with heat stress; squares: unstressed; triangles: 48 hours at 60° C.; circles: 240 hours at 60° C.

It is useful then to begin by using heat-stress data on neat CBDA demonstrating experimental measurement, and exact location, of these important peaks with the CBDA and instrumentation used specifically in this experimental work. Thus, FIG. 2 shows the exemplary effect of heat stress on the 1109 peak, in the unformulated Control, the CBDA-rich extract. Note that outside of this peak the stressed and unstressed data are nearly identical.

Having verified the initial positions of these eight carboxyl-associated peaks experimentally, attention now turns to the behavior of these peaks: a) upon intercalation in an LDH; and b) after stressing the resulting CBDA-LDH intercalate, an embodiment of the present invention. The stressed and unstressed CBDA-LDH intercalate produced in Example 1 were as follows:

Sample A-19: unstressed intercalate produced in Example 1 (simplified to Sample "A" in some figure labels);

Sample S-19: heat-stressed intercalate produced in Example 1 (simplified to Sample "S" in some figure labels), stressed at 60° C. for 72 hours.

In Table 2 below, for neat CBDA and the LDH-intercalate Sample A-19, the eight carboxyl-associated peaks seen in the CBDA spectrum have either shifted to a nearby position that can be reasonably assigned, or, as in the case of the CBDA peak at 1621 cm$^{-1}$, have shifted so far that any assignment must be supported independently, as will be illustrated for the 1621 peak in the text below. The 14 non-carboxyl-associated peaks in the region up to 1800 cm$^{-1}$ are seen below to not shift wavenumber significantly on intercalation, while the strong changes in peak intensities are likely due to the strong effects of the LFH matrix on reflectance/absorbance properties, and milieu changes (electrostatic, dielectric, etc.):

TABLE 2

| Neat CBDA | Sample A-19 | Assigned vibration |
|---|---|---|
| 622 | 622 | $\delta$(COO) |
| 695, 730 | 695, 730 | $\rho$(=C—H) rocking, aromatic |
| 764 | 788 | $\delta$(C=O) carboxyl |
| 818 | 822 | Aromatic CH out-of-plane bend |
| 887 | — | $\delta$(OH . . . O) carboxyl |
| 905 | 909 | Cyclohexenyl out-of-plane bend |
| — | 958? | $\pi$(OM) carboxyl (M is aluminum) |
| 965 | — | $\pi$(OH) carboxyl |
| 1014 | 1021 | $\nu$(C—C) pentyl |
| 1030-1088 | 1039-1070 | Aromatic and vinylidene in-plane bends |
| 1109 | 1100 | $\nu$(C—O [=O or —O—M]) carboxyl |
| 1144 | 1144 | $\delta$(C—H) in-plane, ring |
| 1183, 1192 | 1163 | $\nu$(C—OH) Phenolic 2-OH and/or 4-OH |
| 1244 | — | $\nu$(C—OH) carboxyl |
| 1258 | 1263 | CH$_2$ out-of-plane bend |
| 1302 | — | $\delta$(O—H) Phenolic 2-OH (ortho) |
| 1338 | — | $\delta$(O—H . . . O) carboxyl (H-bonded) |
| 1364 | 1364 | Pentyl $\omega$(CH$_2$) |
| 1377 | 1377 | Pentyl $\omega$(CH$_3$) |
| — | 1395 | $\nu_s$ carboxylate (chemisorbed?) |
| — | 1414 | $\nu_s$ carboxylate (physisorbed?) |
| 1437 | 1437 | $\nu$(C—C) |
| 1456 | 1456 | $\nu$(C—C) ring |
| 1462, 1472 | 1462, 1472 | $\nu$(C—C) ring and $\delta_s$(CH$_2$) |
| 1501 | — | $\nu_s$ carboxyl (H-bonded dimer) |
| 1621 | 1553 | $\nu_{as}$ carboxyl |
| 1580 | 1583 | $\nu$(C=C) ring |
| 1733 | 1744 | $\nu$(C=O) carboxyl |
| 2848 | 2856 | $\nu_s$(C—H) pentyl CH$_2$ |
| 2871 | 2871 | $\nu_{as}$(C—H) CH$_3$ |
| 2920 | 2926 | $\nu_{as}$(C—H) CH$_2$ |
| 2957 | 2957 | $\nu_{as}$(C—H) CH$_3$ |
| — | 3010 | Zn$^{2+}$ carboxylate salt? |
| — | 3452 | LDH Metal-OH (3431 in blank LDH) |
| — | 3575-3620 | OH groups not H-bonded |

The observed peaks for Sample A-19 and for neat CBDA. It should be noted that vibrations involving a carboxyl OH group are not present in Sample A-19 (or present at very weak intensity), thus confirming that the acidic group of the cannabinoid is deprotonated. Similarly, peaks in A-19 assigned to deprotonated or metal-bonded carboxylate groups are not present in neat CBDA. All peak positions are in cm$^{-1}$ wavenumbers.

Figure 3:
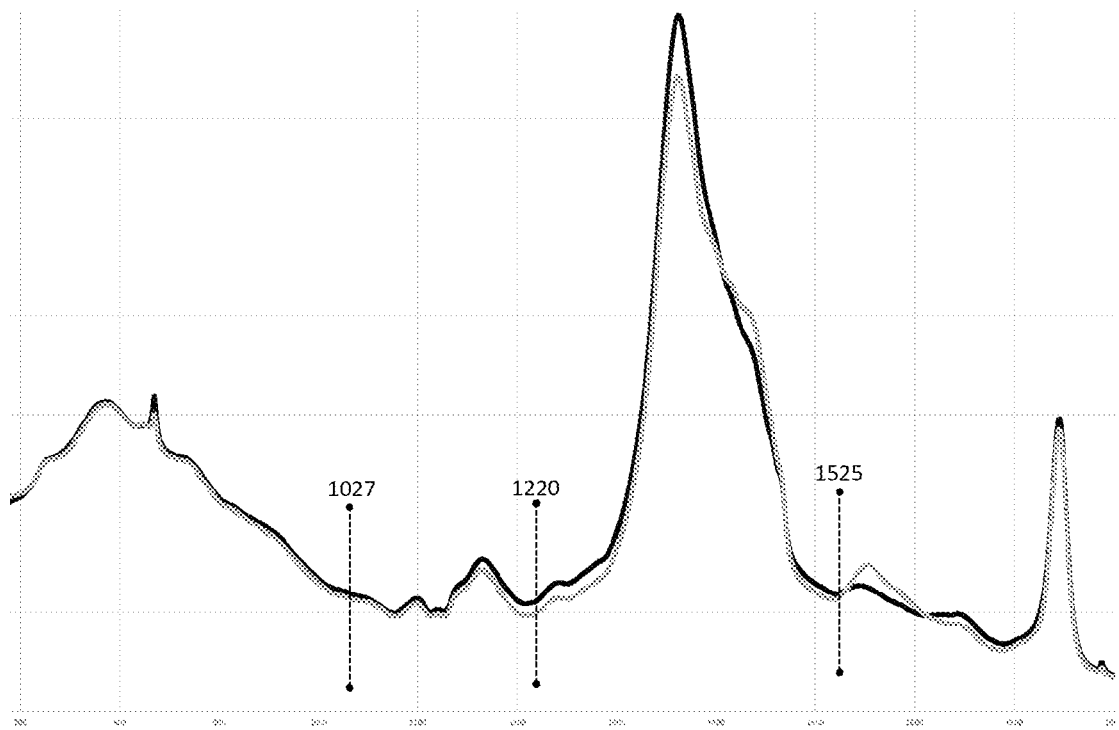
FIG. 3. ATR-FTIR spectra of LDH intercalate Sample A-19 (black curve), and 72-hour heat-stressed Sample S-19 (grey curve), showing absence of substantial peaks at the three most prominent "CBD-Only" degradant positions (3 dashed lines).

Herein, "CBD-Only" peak positions will indicate positions that are observed in spectra of CBD, but not in pure CBDA. The most prominent of these positions are 1027, 1220 and 1525 cm$^{-1}$. FIG. 3 demonstrates the absence of these degradant peaks in Sample A-19 and in the heat-stressed S-19, and it should be borne in mind that all three of these peaks should be present simultaneously were CBD present.

Due to the fact that decarboxylation of CBDA can conform to an oxidative-decarboxylation mechanism and can oxidize to form several quinone degradants that are presently poorly characterized in the open literature, it is important to check the A-19 and S-19 spectra for evidence of quinones such as cannabiquinone. Peak positions expected for a cannabiquinone are 1050, 1150, 1377 and 1643 cm$^{-1}$, and again, all these peaks, termed "Quinone-Only" peaks herein, should be present if the strongly-colored quinones are present. While there is evidence pointing to a small amount of quinone present, the weak intensity of the peaks, most notable at 1050 cm$^{-1}$, together with the absence of pinkish coloration in these samples, indicates a low degree of quinone formation (FIG. 4).

Figure 4:
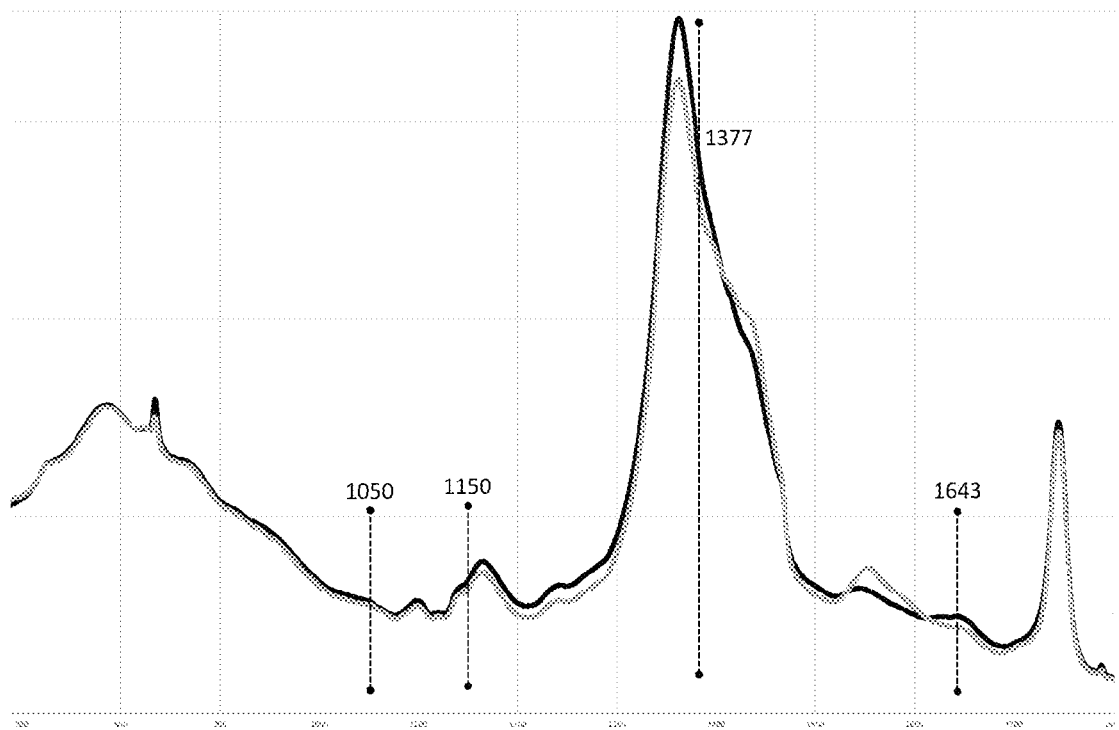
FIG. 4. ATR-FTIR spectra of LDH intercalate Sample A-19 (black curve), and 72-hour heat-stressed Sample S-19 (grey curve), showing weakness or absence of substantial peaks at the four most prominent "Quinone-Only" degradant positions (4 dashed lines).
Figure 5:
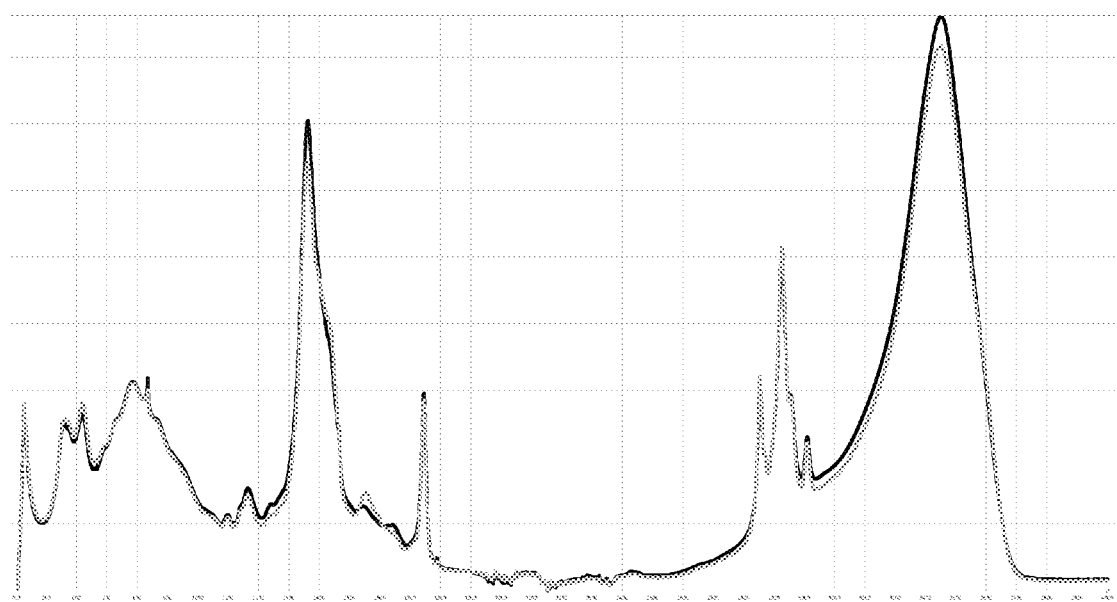
FIG. 5. ATR-FTIR spectra of LDH intercalate Sample A-19 (black curve), and 72-hour heat-stressed Sample S-19 (grey curve) over the entire spectrum measured, showing nearly identical spectra indicating a very low degree of degradation from the 72-hour heat-stress.
Figure 6:
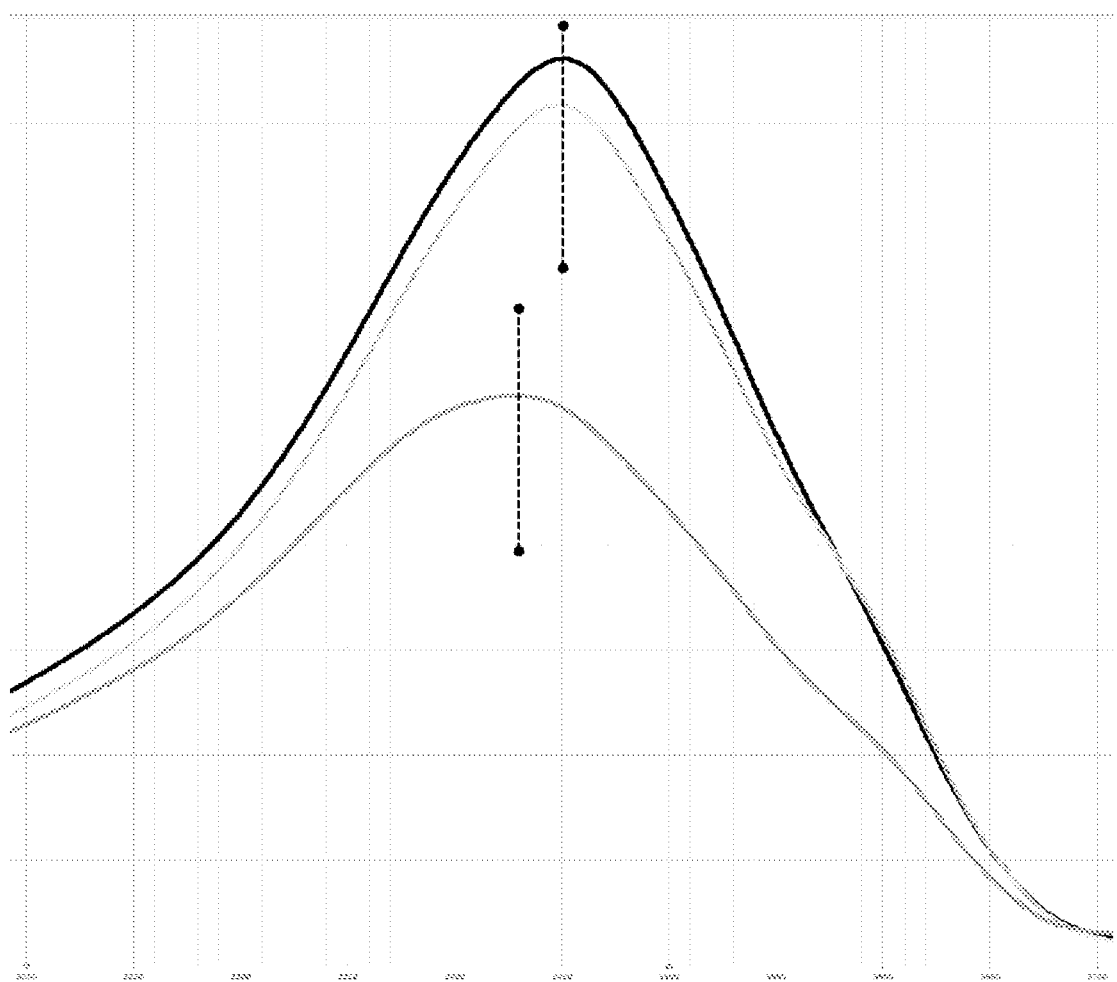
FIG. 6. Close-up of the metal-OH vibration region of the FTIR spectra of Sample A-19 (black curve), stressed Sample S-19 (dotted curve), and the blank LDH matrix (solid grey, lowest curve). A shift from 3431 in the empty LDH to 3450 in both A-19 and S-19 is clearly evident, confirming the effect of the cannabinoid intercalation on the LDH matrix itself.

As negligible decarboxylation to CBD, or to a quinone, is shown in FIG. 4, thus indicating minimal decarboxylation and limited oxidation, it might be expected that the spectra for these stressed and unstressed intercalate samples are very close, and indeed, FIG. 5 shows the very tight relationship between the unstressed Sample A-19 and the heat-stressed S-19 over the entire measured spectrum FTIR explorations of LDH intercalates have generally shown significant shifts in the (rather broad) peaks due to the inorganic LDH matrix itself. In the present case, a shift from about 3431 to 3450 cm$^{-1}$ for empty LDH to both samples A-19 and S-19 indicates a strong electrostatic interaction between CBDA$^-$ ions and the LDH matrix, and once again confirming the tight match between stressed and unstressed intercalate (FIG. 6).

In further work, the empty LDH, that is, without any cannabinoid present, was also heat-stressed for 100 hours at 60° C., upon which zero change in the position of the peak at 3431 cm-1 was observed; in both stressed and unstressed LDH blanks that peak positions were identical at 3431 cm$^{-1}$. This is critically important because it—together with the shift seen for the unstressed sample "A"—demonstrates that the shift in this peak was not due to heat-stress, but rather to the effect of the intercalated acidic cannabinoid.

This is also consistent with the change in the well-known carboxylate parameter $\Delta = \nu_{as} - \nu_s$. This parameter is known to be correlated with changes in the state of the carboxyl group. For our Control unformulated CBDA, $\Delta = 1621 - 1501 = 120$ cm$^{-1}$; it is known that values for carboxylates in the protonated dimer configuration are usually very near 121 cm$^{-1}$. So, the Control 91% CBDA fits the usual $\nu_{as}|\nu_s$ split common for organic carboxylic acids. In sharp contrast, the intercalated CBDA shows a strong shift of Vas to 1553, and one apparent $n_s$ peak at 1395 that yields $\Delta = 1553 - 1395 = 158$ cm$^{-1}$, together with a second apparent peak at 1414 yielding $\Delta = 1553 - 1414 = 139$ cm$^{-1}$. Interestingly, this pattern of $\Delta$-values mimics quantitatively the $\Delta$-values that have been reported for monovalent Cu$^{1+}$ (cuprous; Cu(I)) ions adsorbed to an acetate carboxylate group, where a measured $\Delta = 139$ cm$^{-1}$ was interpreted as due to monodentate chemisorbed ions, and $\Delta = 159$ cm$^{-1}$ was interpreted as due to monodentate physisorbed ions. Because the aluminum ions in the LDH matrix are predominantly in the 1+ valence form, the cuprous-carboxylate interaction is very relevant to the present case reported herein. It should also be noted that the peak near $\Delta = 1437$ cm$^{-1}$, is assignable to $\nu$(C—C) of carbon ring structures. As is generally agreed in the literature, bond energy above about 0.5 eV or 48 kJ/mol is the dividing line from physiosorption into chemisorption, and indeed the chemisorbed cuprous-carboxylate bond has been reported to have a bond energy very close to 50 kJ/mol.

Without wishing to be bound by theory, the presence of cannabidiolate anions chemisorbed to aluminum ions in the LDH could explain the powerful stabilizing effect of the LDH matrix on the very carboxylate that is bound, for at least 2 reasons. First, because the LDH is selective as to the chemical species that can diffuse readily inside the matrix, it may be excluding degrading species such as diatomic (or other forms of) oxygen, 'other' heavy metal contaminants, or other organics. And second, for many reasons, strongly binding the carboxylate group may interfere with decarboxylation of CBDA sterically or by the effects of the strong electrostatic interaction on CBDA reactivity. As is known from other stabilization methodologies (see, e.g., U.S. Pat. No. 8,858,927 to Anderson, the complete contents of which is hereby incorporated by reference in entirety), the additional presence of another species—here, possibly, physiosorbed cannabidiolate—can create a 'flickering' or intermittent bond that provides sufficient stabilization without crystallization in one form, which, if even possible, might be expected to hinder release of the active.

In some embodiments of the present invention, a value of delta ($\Delta = v_{as} - v_s$) obtained by subtracting the position of the peak for one symmetric carboxyl vibration vs from that of the asymmetric carboxyl vibration Vas as measured by FTIR is between about 130 and 148 $cm^{-1}$ at ambient temperature, and in some embodiments between about 135 and 143 $cm^{-1}$, and in some embodiments between about 137 and 141 $cm^{-1}$.

In some embodiments of the present invention, one value of delta ($\Delta = v_{as} - v_s$) is between about 130 and 148 $cm^{-1}$ at ambient temperature, indicating significant albeit transient chemisorption of the acidic cannabinoid, and a second value of D is also present in the same spectrum between about 150 and 175 $cm^{-1}$ indicating significant albeit transient physisorption of the acidic cannabinoid.

In some embodiments of the present invention, one value of delta ($\Delta = v_{as} - v_s$) is between about 135 and 143 $cm^{-1}$ at ambient temperature, indicating significant albeit transient chemisorption of the acidic cannabinoid, and a second value of D is also present in the same spectrum between about 150 and 175 $cm^{-1}$ indicating significant albeit transient physisorption of the acidic cannabinoid. This is an indication of ongoing shifting, or "flickering", between physisorbed and chemisorbed states of bonding between the acidic cannabinoid, on a timescale that is slower than the timescale associated with the actual vibration itself (said timescale corresponding to at least several periods of the vibration). Other measurements, such as NMR, indicating this unusual and surprising state of bonding may also or alternatively be used to establish the presence of the present invention in a composition comprising an acidic cannabinoid and a layered double-hydroxide.

As seen from Table 2, the value of delta for neat CBDA is $v_{as} - v_s = 1621 - 1501 = 120$ $cm^{-1}$. It is no coincidence that this is the value associated with H-bonded carboxylic acids, that is, in their protonated and dimer form. This is exactly as expected for cannabidiolic acid in neat form.

This FTIR analysis thus shows:
No significant changes in peak positions over the entire spectrum after 72 hours at 60° C., and only minor changes in peak intensities;
CBDA non-carboxylate peaks all present and accounted for, unshifted, in spectra of both unstressed Sample A-19 and stressed Sample S-19;
Spectra show no systematic presence of "CBD-only" degradant peaks;
Spectra show no systematic presence of CBQ quinone degradant peaks;
Spectra show no systematic presence of MCT residual solvent peaks;
Spectra indicate low levels of inorganic residuals (nitrates, carbonates, etc.);
Shift-to positions of carboxylate-specific peaks, specifically the symmetric and asymmetric carboxyl vibrations $v_s$ and $v_{as}$, have been identified and fit fairly closely to known positions for monovalent metal cation ($Cu^{1+}$)—carboxylate bond positions;
There is evidence for monodentate binding that is borderline chemisorption.

In summary, this analysis shows that one embodiment of this invention, namely a composition comprising an acidic cannabinoid intercalated within the gallery of a zinc-aluminum layered double-hydroxide, with a molar zinc:aluminum ratio of about 3, and exhibiting FTIR peaks yielding both a delta value of about 139 $cm^{-1}$ consistent with monodentate chemisorption and another delta value of about 158 $cm^{-1}$ consistent with monodentate physisorption, provides protection of the cannabinoid from both oxidation and decarboxylation thus resulting in dramatically improved stability. That result is also consistent with the TLC analysis herein, as well as the colorimetry also shown herein. As used herein as well as in FTIR analysis of carboxylates in general, delta is $D = n_{as} - n_s$.

Example 5

Several colorimetric measurements were made on the powdered CBDA-LDH intercalate produced in Example 1 above.

The Fast Blue BB test is a well-established marker for cannabinoids, yielding a deep reddish color in seconds for CBD, and a strong orange or yellow-orange color in seconds for CBDA (or several minutes when the cannabinoid is on a TLC plate). This was confirmed for CBD and CBDA standards using Fast Blue BB hemi(zinc chloride) salt, then the colorimetric test applied to the intercalate, which was dispersed lightly in aqueous reagent for this tests. As seen from the Table below, the deep coloration in the powder (at the bottom of the test tube upon settling) developed only very slowly, over a period of 2 weeks, as shown in Table 3.

TABLE 3

| Reaction time (hours) | Hex color code | C\|M\|Y\|K |
| --- | --- | --- |
| 3 | #c79949 | 0 \| 23 \| 63 \| 22 |
| 17 | #cc9534 | 0 \| 27 \| 75 \| 20 |
| 120 | #d87b23 | 0 \| 43 \| 88 \| 15 |
| 336 | #7a2a03 | 0 \| 66 \| 98 \| 52 |

Color analysis of powder of the invention when reacted with Fast Blue BB, demonstrating the extremely slow reaction of Fast BB dye with a CBDA-LDH intercalate of the invention, taking several weeks, as compared to the usual seconds reaction time in a simple solution of CBDA. This demonstrates that the CBDA is primarily buried in the gallery regions of the intercalated powder, such that the dye can migrate only very slowly to reach, and react with, the cannabidiolate, or the cannabidiolate migrate toward the surface of a particle to become more accessible to the dye. Ferric chloride test.

The well-known ferric chloride test for cannabinoids does not require compounds with higher MW such as the dye used above (MW~ 416), and most importantly in the context of this invention, tests for protection against oxidation. Neat CBDA produces a yellow or pinkish-yellow discoloration, with the pink (represented by a significant Magenta value in CMYK value) emanating mostly from quinones produced by oxidation of the cannabinoid. Indeed in this test, the neat CBDA standard produced a strong coloration, with color code #ffb159, corresponding to CMYK=0|31|65|0. In contrast, the ferric chloride test was applied to a CBDA-LDH intercalate powder of the invention, and yielded only a minor color change #cabe81, corresponding to CMYK=0 6|36|21, clearly demonstrating a much lower Yellow (/Magenta) discloration. This test thus demonstrates that strong oxidizers such as ferric chloride are only able to oxidize formulated CBDA at a rate that is much slower than unformulated CBDA.

Example 6

A path for establishing a CBDA-based product of the invention, for transdermal sustained-release delivery of CBDA in the treatment of epilepsy (and other spasticities), will be described for the case where a washable garment is used as the delivery vehicle. This type of vehicle has been patented (see U.S. Pat. No. 9,669,012 to Anderson et al., the complete contents of which is hereby incorporated by referenced in entirety) and commercialized in several formats currently including socks, compression risk and knee sleeves, and while similar in some ways to a transdermal patch, the vehicle differs fundamentally in many ways from a patch, such as being breathable (non-occlusive), dry, comfortable, pleasant looking, part of normal daily routine, and washable in a standard washing machine cycle. The manufacture would consist of first milling the powder—here the dry CBDA-LDH intercalate made as described herein—conveniently to a particle size of 5-50 microns, and then following the processes and practices delineated in the line of patents from 9,669,012: dispersing the milled powder in a (viscous) polymerizable liquid such as a monomer or prepolymer for a period long enough to allow polymerization to the point of dryness; the dispersion (or suspension) is applied to a yarn of choice, with nylon being most commonly used, and immediately polymerized (or crosslinked, in the case of a prepolymer or crosslinkable gum). At the time of this writing, initiation via ultraviolet light is most common, and recalling that the present disclosure demonstrates strong protection of the intercalated CBDA from light and (at least certain) oxidative conditions, this initiation method can be expected to cause only modest degradation of the CBDA; and by selecting prepolymers of relatively high molecular weight (roughly 3,000-10,000 MW), the required UV exposure can be made short; furthermore, as discussed herein there are commercially available radical scavengers that can be intercalated along with the CBDA, minimizing their effect on the matrix reaction. Besides UV, another possible polymerization method is through the use of liquids that polymerize upon contact with humidity in the air; other mild chemistries are available for crosslinking prepolymers of myriad types. This can be performed while maintaining the physical properties (including strong adhesion of polymer to the yarn) required for garment knitting using standard industrial equipment, so that the yarn containing embedded CBDA-LDH particles of the current invention is knitted into a compression sleeve, which then delivers CBDA to the skin in contact with the sleeve. Established in vitro and non-mammalian in vivo screening methods that are strongly predictive for anticonvulsant effects in a human or mammal are known from academic and patent literature, such as the Dictyostelium discoideum based screen which uses that genus of amoeba, described in the above-cited US App. 20180228751 to Stott. Such tests can be applied to the intercalated and milled embodiment of the current invention. Lennox-Gastaut syndrome in children might be an excellent indication for this embodiment because the parent can be sure the child is obtaining a steady dosing of CBDA by simply having the child wear the garment—as opposed to arranging for adult supervision of midday pills- and CBDA has been shown to have very high potency in these indications.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

I claim:
1. A particulate material,
wherein at least some particles in the particulate material are layered double hydroxide (LDH) particles having a general formula

$$MII_{1-x}MIII_x(OH)_2(C^{1-})_x \cdot mH_2O$$

wherein
x is from 0.1 to 0.4;
m is from 0 to 0.50;
MII is $Zn^{2+}$;
MIII is $Al^{3+}$; and
$C^{1-}$ is a carboxylated cannabinoid selected from the group consisting of cannabidiolic acid (CBDA), tetrahydrocannabinolic acid (THCA), cannabigerolic acid (CBGA), and olivetolic acid;
and wherein a portion of the carboxylated cannabinoid is intercalated within the LDH particles and retained therein in a non-degraded carboxylated form,
wherein the portion of the carboxylated cannabinoid that is retained in non-degraded carboxylated form is at least 50% when the particulate material is maintained at 25° C. for 6 months.
2. A powder of the particulate material of claim 1, wherein said at least some particles of the particulate material have a primary crystallite size of less than 5 microns and/or a diameter or a largest dimension ranging from 0.1 to 100 microns.
3. The particulate material of claim 1, wherein the $C^{1-}$ is CBDA.
4. A tablet comprising the particulate material of claim 3.
5. The particulate material of claim 1 wherein the particulate material is in the form of a free-flowing powder.
6. A composition, comprising
the particulate material of claim 1, and
a carrier.
7. The composition of claim 6 wherein the carrier is a beverage.
8. The composition of claim 6 wherein the carrier is a tablet.
9. The composition of claim 6 wherein the carrier is selected from the group consisting of a gas propellant, a cream, a lotion, an ointment, eye drops, an oral solution, an otic solution, a suppository, an injectable solution, a cosmetic, a vaginally deliverable solution, and a garment.
10. The composition of claim 1, wherein x ranges from 0.25 to 0.33.
11. The composition of claim 1, wherein the portion of the carboxylated cannabinoid that is retained in non-degraded form is at least 90% when the particulate material is maintained at 25° C. for 6 months.
12. A particulate material,
wherein at least some particles in the particulate material are layered double hydroxide (LDH) particles having a general formula $$MII_{1-x}MIII_x(OH)_2(C^{1-})_x \cdot mH_2O$$

wherein
x is from 0.1 to 0.4;
m is from 0 to 0.50;
MII is $Zn^{2+}$;
MIII is $Al^{3+}$; and
$C^{1-}$ is a carboxylated cannabinoid selected from the group consisting of cannabidiolic acid (CBDA), tetrahydrocannabinolic acid (THCA), cannabigerolic acid (CBGA), and olivetolic acid;

wherein a portion of the carboxylated cannabinoid is intercalated within the LDH particles and retained therein in a carboxylated, non-degraded form.

13. The particulate material of claim 12, wherein the $C^{1-}$ is CBDA.

14. The particulate material of claim 12, wherein the portion of the carboxylated cannabinoid that is retained in a carboxylated, non-degraded form is at least 90% when maintained at 25° C. for 6 months.

15. A particulate material,
wherein at least some particles in the particulate material are layered double hydroxide (LDH) particles having a general formula $$MII_{1-x}MIII_x(OH)_2(C^{1-})_x \cdot mH_2O$$

wherein
x is from 0.1 to 0.4;
m is from 0 to 0.50;
MII is $Zn^{2+}$; and
MIII is $Al^{3+}$; and
$C^{1-}$ is a carboxylated cannabinoid selected from the group consisting of cannabidiolic acid (CBDA), tetrahydrocannabinolic acid (THCA), cannabigerolic acid (CBGA), and olivetolic acid;
wherein a portion of the carboxylated cannabinoid is intercalated within the LDH particles and bonded thereto.

16. The particulate material of claim 15, wherein the carboxylated cannabinoid is CBDA.

17. A particulate material,
wherein at least some particles in the particulate material are layered double hydroxide (LDH) particles having a general formula $$MII_{1-x}MIII_x(OH)_2(C^{1-})_x \cdot mH_2O$$

wherein
x is from 0.1 to 0.4;
m is from 0 to 0.50;
MII is $Zn^{2+}$;
MIII is $Al^{3+}$; and
$C^{1-}$ is a carboxylated cannabinoid having an acidic group and a carboxylate group and selected from the group consisting of cannabidiolic acid (CBDA), tetrahydrocannabinolic acid (THCA), cannabigerolic acid (CBGA), and olivetolic acid;
and wherein the acidic group of the cannabinoid is deprotonated and the carboxylate group is metal-bonded with MII or MIII.

18. The particulate material of claim 17, wherein the carboxylated cannabinoid is CBDA.

* * * * *